(12) United States Patent
Doxey et al.

(10) Patent No.: US 10,258,564 B2
(45) Date of Patent: Apr. 16, 2019

(54) TOPICAL COMPOSITIONS AND METHODS OF USING THE SAME

(71) Applicant: Novan, Inc., Durham, NC (US)

(72) Inventors: Ryan Doxey, Raleigh, NC (US); Adam Sabouni, Cary, NC (US); Eleftherios Kougoulos, Morrisville, NC (US); Nathan Stasko, Durham, NC (US)

(73) Assignee: Novan, Inc., Morrisville, NC (US)

( * ) Notice: Subject to any disclaimer, the term of this patent is extended or adjusted under 35 U.S.C. 154(b) by 267 days.

(21) Appl. No.: 14/771,138

(22) PCT Filed: Feb. 28, 2014

(86) PCT No.: PCT/US2014/019536
§ 371 (c)(1),
(2) Date: Aug. 27, 2015

(87) PCT Pub. No.: WO2014/134502
PCT Pub. Date: Sep. 4, 2014

(65) Prior Publication Data
US 2016/0008275 A1   Jan. 14, 2016

Related U.S. Application Data

(60) Provisional application No. 61/770,615, filed on Feb. 28, 2013.

(51) Int. Cl.
| | |
|---|---|
| *A61K 9/00* | (2006.01) |
| *A61K 47/10* | (2017.01) |
| *A61K 47/12* | (2006.01) |
| *A61K 9/06* | (2006.01) |
| *A61K 47/32* | (2006.01) |
| *A61K 33/00* | (2006.01) |
| *A61K 47/69* | (2017.01) |

(52) U.S. Cl.
CPC .......... *A61K 9/0014* (2013.01); *A61K 9/06* (2013.01); *A61K 33/00* (2013.01); *A61K 47/10* (2013.01); *A61K 47/12* (2013.01); *A61K 47/32* (2013.01); *A61K 47/6923* (2017.08)

(58) Field of Classification Search
CPC combination set(s) only.
See application file for complete search history.

(56) References Cited

U.S. PATENT DOCUMENTS

| | | |
|---|---|---|
| 3,754,368 A | 8/1973 | Moore et al. |
| 4,182,827 A | 1/1980 | Jones et al. |
| 4,829,092 A | 5/1989 | Nelson et al. |
| 4,917,886 A | 4/1990 | Asche et al. |
| 5,405,919 A | 4/1995 | Keefer |
| 5,519,020 A | 5/1996 | Smith et al. |
| 5,691,423 A | 11/1997 | Smith et al. |
| 5,770,645 A | 6/1998 | Stamler et al. |
| 5,814,656 A | 9/1998 | Saavedra et al. |
| 5,814,666 A | 9/1998 | Green et al. |
| 5,840,759 A | 11/1998 | Mitchell et al. |
| 5,910,316 A | 6/1999 | Keefer et al. |
| 5,912,008 A | 6/1999 | Horstmann et al. |
| 5,958,427 A | 9/1999 | Salzman et al. |
| 5,968,001 A | 10/1999 | Freeman |
| 5,968,528 A | 10/1999 | Deckner et al. |
| 6,103,266 A | 8/2000 | Tapolsky et al. |
| 6,103,275 A | 8/2000 | Seitz et al. |
| 6,110,453 A | 8/2000 | Keefer et al. |
| 6,303,141 B1 | 10/2001 | Fischer et al. |
| 6,319,913 B1 * | 11/2001 | Mak .............. A61K 9/0014 514/179 |
| 6,382,526 B1 | 5/2002 | Reneker et al. |
| 6,465,445 B1 | 10/2002 | Labrie |
| 6,479,058 B1 * | 11/2002 | McCadden ............. A61K 8/19 424/401 |
| 6,520,425 B1 | 2/2003 | Reneker |
| 6,695,992 B2 | 2/2004 | Reneker |
| 6,719,997 B2 | 4/2004 | Hsu et al. |
| 6,737,447 B1 | 5/2004 | Smith et al. |
| 6,818,018 B1 | 11/2004 | Sawhney |
| 6,861,064 B1 | 3/2005 | Laakso et al. |
| 7,048,951 B1 | 5/2006 | Seitz et al. |
| 7,704,518 B2 | 4/2010 | Tamarkin et al. |
| 8,241,650 B2 | 8/2012 | Peters |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,486,451 B2 | 7/2013 | Morris et al. |
| 8,591,876 B2 | 11/2013 | Bauman et al. |
| 8,617,100 B2 | 12/2013 | Eini et al. |
| 8,636,982 B2 | 1/2014 | Tamarkin et al. |
| 8,722,103 B2 | 5/2014 | Morris et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |

(Continued)

FOREIGN PATENT DOCUMENTS

| | | |
|---|---|---|
| CA | 2 594 407 A1 | 8/2006 |
| EP | 1 300 424 A1 | 4/2003 |

(Continued)

OTHER PUBLICATIONS

Extended European Search Report corresponding to European Patent Application No. 14756266.4 (6 pages) (dated Aug. 2, 2016).

(Continued)

*Primary Examiner* — Sean M Basquill
(74) *Attorney, Agent, or Firm* — Myers Bigel, P.A.

(57) ABSTRACT

The present invention relates generally to compositions and methods of using the same. A first aspect of the present invention comprises a composition comprising a first viscosity increasing agent; at least one polyhydric alcohol; at least one buffering agent; at least one preservative; a second viscosity increasing agent; at least one organic solvent; at least one humectant; at least one active pharmaceutical ingredient; and water, wherein the composition is buffered to a pH of about 3 to about 11.

19 Claims, 12 Drawing Sheets

(56) References Cited

U.S. PATENT DOCUMENTS

| | | | |
|---|---|---|---|
| 9,101,662 B2 | 8/2015 | Tamarkin et al. | |
| 9,161,916 B2 | 10/2015 | Tamarkin et al. | |
| 9,265,725 B2 | 2/2016 | Tamarkin et al. | |
| 9,320,705 B2 | 4/2016 | Tamarkin et al. | |
| 2002/0012816 A1 | 1/2002 | Shimizu et al. | |
| 2002/0013304 A1 | 1/2002 | Wilson et al. | |
| 2002/0028223 A1 | 3/2002 | Vatter et al. | |
| 2002/0082221 A1 | 6/2002 | Herrmann et al. | |
| 2002/0094985 A1 | 7/2002 | Herrmann et al. | |
| 2002/0122771 A1 | 9/2002 | Holland et al. | |
| 2002/0136750 A1 | 9/2002 | Benjamin et al. | |
| 2002/0155174 A1 | 10/2002 | Benjamin et al. | |
| 2003/0077243 A1 | 4/2003 | Fitzhugh | |
| 2003/0159702 A1 | 8/2003 | Lindell et al. | |
| 2003/0175328 A1 | 9/2003 | Shefer et al. | |
| 2003/0205234 A1 | 11/2003 | Bardach et al. | |
| 2003/0235605 A1 | 12/2003 | Lelah et al. | |
| 2004/0009238 A1 | 1/2004 | Miller et al. | |
| 2004/0043068 A1 | 3/2004 | Tedeschi et al. | |
| 2004/0068005 A1 | 4/2004 | Szilvassy et al. | |
| 2004/0171589 A1 | 9/2004 | Herrmann et al. | |
| 2004/0202684 A1 | 10/2004 | Djerassi | |
| 2004/0220260 A1 | 11/2004 | Cals-Grierson | |
| 2004/0265244 A1 | 12/2004 | Rosen | |
| 2005/0038473 A1 | 2/2005 | Tamarkin et al. | |
| 2005/0232869 A1 | 10/2005 | Tamarkin et al. | |
| 2005/0271596 A1 | 12/2005 | Friedman et al. | |
| 2006/0159734 A1 | 7/2006 | Shudo | |
| 2006/0160897 A1 | 7/2006 | Pelicci et al. | |
| 2006/0173076 A1 | 8/2006 | Vishnupad et al. | |
| 2006/0269620 A1 | 11/2006 | Morris et al. | |
| 2006/0275218 A1 | 12/2006 | Tamarkin et al. | |
| 2007/0166255 A1 | 7/2007 | Gupta | |
| 2007/0243224 A1 | 10/2007 | Ludwig et al. | |
| 2007/0292359 A1 | 12/2007 | Friedman et al. | |
| 2007/0292461 A1 | 12/2007 | Tamarkin et al. | |
| 2008/0031907 A1 | 2/2008 | Tamarkin et al. | |
| 2008/0044444 A1 | 2/2008 | Tamarkin et al. | |
| 2008/0063607 A1 | 3/2008 | Tamarkin et al. | |
| 2008/0069779 A1 | 3/2008 | Tamarkin et al. | |
| 2008/0071206 A1 | 3/2008 | Peters | |
| 2008/0138296 A1 | 6/2008 | Tamarkin et al. | |
| 2008/0152596 A1 | 6/2008 | Friedman et al. | |
| 2008/0166303 A1 | 7/2008 | Tamarkin et al. | |
| 2008/0206155 A1 | 8/2008 | Tamarkin et al. | |
| 2008/0206159 A1 | 8/2008 | Tamarkin et al. | |
| 2008/0206161 A1 | 8/2008 | Tamarkin et al. | |
| 2008/0253973 A1 | 10/2008 | Tamarkin et al. | |
| 2008/0260655 A1 | 10/2008 | Tamarkin et al. | |
| 2008/0292560 A1 | 11/2008 | Tamarkin et al. | |
| 2008/0299220 A1 | 12/2008 | Tamarkin et al. | |
| 2008/0311163 A1 | 12/2008 | Peters | |
| 2008/0317679 A1 | 12/2008 | Tamarkin et al. | |
| 2009/0041680 A1 | 2/2009 | Tamarkin et al. | |
| 2009/0068118 A1 | 3/2009 | Eini et al. | |
| 2009/0068248 A1 | 3/2009 | Waterhouse et al. | |
| 2009/0130029 A1 | 5/2009 | Tamarkin et al. | |
| 2009/0175799 A1 | 7/2009 | Tamarkin et al. | |
| 2009/0214618 A1 | 8/2009 | Schoenfisch et al. | |
| 2009/0226380 A1 | 9/2009 | Clark et al. | |
| 2009/0297634 A1 | 12/2009 | Friedman et al. | |
| 2010/0098733 A1* | 4/2010 | Stasko | A61K 8/19 424/401 |
| 2010/0221195 A1 | 9/2010 | Tamarkin et al. | |
| 2010/0266510 A1 | 10/2010 | Tamarkin et al. | |
| 2010/0286285 A1 | 11/2010 | Barthez et al. | |
| 2010/0310476 A1 | 12/2010 | Tamarkin et al. | |
| 2010/0331968 A1 | 12/2010 | Morris et al. | |
| 2011/0027369 A1 | 2/2011 | Franke | |
| 2011/0045037 A1 | 2/2011 | Tamarkin et al. | |
| 2011/0052650 A1 | 3/2011 | Morris et al. | |
| 2011/0082167 A1 | 4/2011 | Pisak et al. | |
| 2011/0086234 A1 | 4/2011 | Stasko et al. | |
| 2011/0097279 A1 | 4/2011 | Tamarkin et al. | |
| 2011/0212033 A1 | 9/2011 | Tamarkin et al. | |
| 2011/0263526 A1 | 10/2011 | Satyam | |
| 2012/0021055 A1* | 1/2012 | Schoenfisch | A61K 9/167 424/489 |
| 2012/0114547 A1 | 5/2012 | Smith | |
| 2012/0134951 A1 | 5/2012 | Stasko et al. | |
| 2012/0136323 A1 | 5/2012 | Stasko et al. | |
| 2012/0141384 A1 | 6/2012 | Tamarkin et al. | |
| 2012/0156163 A1 | 6/2012 | Bauman et al. | |
| 2012/0230921 A1* | 9/2012 | Stasko | A61K 8/19 424/49 |
| 2012/0237453 A1 | 9/2012 | Tamarkin et al. | |
| 2013/0059017 A1 | 3/2013 | Perricone et al. | |
| 2013/0109756 A1 | 5/2013 | Huber et al. | |
| 2013/0164225 A1 | 6/2013 | Tamarkin et al. | |
| 2013/0189191 A1 | 7/2013 | Tamarkin et al. | |
| 2013/0189193 A1 | 7/2013 | Tamarkin et al. | |
| 2013/0189195 A1 | 7/2013 | Tamarkin et al. | |
| 2013/0310533 A1 | 11/2013 | Bao et al. | |
| 2013/0344334 A1 | 12/2013 | Schoenfisch et al. | |
| 2014/0017121 A1 | 1/2014 | Schoenfisch et al. | |
| 2014/0057001 A1 | 2/2014 | Bauman et al. | |
| 2014/0058124 A1 | 2/2014 | Schoenfisch et al. | |
| 2014/0065200 A1 | 3/2014 | Schoenfisch et al. | |
| 2014/0107071 A1 | 4/2014 | Kougoulos et al. | |
| 2014/0134321 A1 | 5/2014 | Stasko et al. | |
| 2014/0171395 A1 | 6/2014 | Schoenfisch et al. | |
| 2014/0193502 A1 | 7/2014 | Tamarkin et al. | |
| 2014/0242023 A1 | 8/2014 | Doxey et al. | |
| 2014/0248219 A1 | 9/2014 | Tamarkin et al. | |
| 2014/0255318 A1 | 9/2014 | Stasko et al. | |
| 2014/0271494 A1 | 9/2014 | Tamarkin et al. | |
| 2014/0369949 A1 | 12/2014 | Peters | |
| 2015/0017103 A1 | 1/2015 | Tamarkin et al. | |
| 2015/0024052 A1 | 1/2015 | Doxey | |
| 2015/0025060 A1 | 1/2015 | Tamarkin et al. | |
| 2015/0111973 A1 | 4/2015 | Bauman et al. | |
| 2015/0118164 A1 | 4/2015 | Tamarkin et al. | |
| 2015/0141606 A1 | 5/2015 | Bao et al. | |
| 2015/0182543 A1 | 7/2015 | Schoenfisch et al. | |
| 2015/0225488 A1 | 8/2015 | Schoenfisch et al. | |

FOREIGN PATENT DOCUMENTS

| | | |
|---|---|---|
| EP | 1 707 224 A1 | 10/2006 |
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| GB | 2 354 441 | 3/2001 |
| JP | H07-039748 | 2/1995 |
| JP | 2002-531526 | 9/2002 |
| JP | 2003-286153 | 10/2003 |
| JP | 2012-197300 | 10/2012 |
| WO | WO 93/10754 A1 | 6/1993 |
| WO | WO 96/13164 A1 | 5/1996 |
| WO | WO 96/15797 A1 | 5/1996 |
| WO | WO 98/05689 A1 | 2/1998 |
| WO | WO 2000/002593 A2 | 1/2000 |
| WO | WO 00/33877 A1 | 6/2000 |
| WO | WO 00/49993 A2 | 8/2000 |
| WO | WO 01/21148 A1 | 3/2001 |
| WO | WO 01/26702 A2 | 4/2001 |
| WO | WO 01/85013 A2 | 11/2001 |
| WO | WO 02/020026 A2 | 3/2002 |
| WO | WO 02/41902 A1 | 5/2002 |
| WO | WO 02/056864 A2 | 7/2002 |
| WO | WO 03/013489 A1 | 2/2003 |
| WO | WO 03/072039 A2 | 9/2003 |
| WO | WO 03/078437 A1 | 9/2003 |
| WO | WO 03/086282 A2 | 10/2003 |
| WO | WO 03/092763 A1 | 11/2003 |
| WO | WO 2004/012659 A2 | 2/2004 |
| WO | WO 2004/012874 A1 | 2/2004 |
| WO | WO 2004/098538 A2 | 11/2004 |
| WO | WO 2005/003032 A1 | 1/2005 |
| WO | WO 2005/004984 A1 | 1/2005 |

(56) References Cited

FOREIGN PATENT DOCUMENTS

| | | |
|---|---|---|
| WO | WO 2005/011575 A2 | 2/2005 |
| WO | WO 2005/037339 A1 | 4/2005 |
| WO | WO 2005/046661 A2 | 5/2005 |
| WO | WO 2006/084910 A2 | 8/2006 |
| WO | WO 2006/084912 A1 | 8/2006 |
| WO | WO 2006/100154 A1 | 9/2006 |
| WO | WO 2006/128121 A2 | 11/2006 |
| WO | WO 2006/138035 A1 | 12/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2007/085254 A1 | 8/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/067095 A1 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2009/131931 A1 | 10/2009 |
| WO | WO 2011/005846 A1 | 1/2011 |
| WO | WO 2011/022652 A1 | 2/2011 |
| WO | WO 2011/022680 A2 | 2/2011 |
| WO | WO-2011022652 A1 * | 2/2011 ........... A61K 9/0014 |
| WO | WO 2011/061519 A2 | 5/2011 |
| WO | WO 2011/073998 A1 | 6/2011 |
| WO | WO 2012/100174 A1 | 7/2012 |
| WO | WO 2012/153331 A2 | 11/2012 |
| WO | WO2013/005508 * | 1/2013 ............... A61K 9/16 |
| WO | WO 2013/006608 A1 | 1/2013 |
| WO | WO 2013/006613 A1 | 1/2013 |
| WO | WO-2013006608 A1 * | 1/2013 ........... A61K 9/0014 |
| WO | WO 2013/138073 A1 | 9/2013 |
| WO | WO 2013/138075 A1 | 9/2013 |
| WO | WO 2015/021382 A2 | 2/2015 |

OTHER PUBLICATIONS

Office Action issued for related Chinese Patent Application No. 201480023840.8 (31 pages) (dated Jul. 31, 2017).
International Preliminary Report on Patentability corresponding to International Patent Application No. PCT/US2014/019536 (13 pages) (dated Sep. 11, 2015).
U.S. Appl. No. 14/191,958, filed Feb. 27, 2014, Doxey et al.

Peyrot et al. English Machine Translation of International Patent Application Publication No. WO 2000/002593 Espacenet (6 pages) (Retrieved on Sep. 27, 2016).
Kandavilli et al. "Polymers in Transdermal Drug Delivery Systems" *Pharmaceutical Technology* pp. 62-80 (2002).
Office Action issued for related Japanese Patent Application No. 2015-560366 (9 pages) (dated Sep. 15, 2017).
Al-Sa'Doni et al. "S-Nitrosothiols: a class of nitric oxide-donor drugs" *Clinical Science* 98:507-520 (2000).
Hrabie et al. "Chemistry of the Nitric Oxide-Releasing Diazeniumdiolate ("Nitrosohydroxylamine") Functional Group and Its Oxygen-Substituted Derivatives" *Chemical Reviews* 102:1135-1154 (2002).
Pulfer et al. "Incorporation of nitric oxide-releasing crosslinked polyethyleneimine microspheres into vascular grafts" *Journal of Biomedical Materials Research* 37:182-189 (1997).
Sangster, James "Octanol-Water Partition Coefficients of Simple Organic Compounds" *Journal of Physical and Chemical Reference Data* 18(3):1111-1227 (1989).
Smith et al. "Transdermal delivery of nitric oxide from diazeniumdiolates" *Journal of Controlled Release* 51:153-159 (1998).
Wang et al. "Nitric Oxide Donors: Chemical Activities and Biological Applications" *Chemical Reviews* 102:1091-1134 (2002).
Boykin et al. "HBO Mediates Increased Nitric Oxide Production Associated With Wound Healing" *Wound Repaid and Regeneration* 12(2):A15 (Abstract 054) (2004).
Final Office Action corresponding to U.S. Appl. No. 14/191,958 (33 pages) (dated May 4, 2016).
U.S. Appl. No. 14/133,973, filed Dec. 19, 2013, Kougoulos et al.
Amadeu et al. "Nitric Oxide Donor Improves Healing if Applied on Inflammatory and Proliferative Phase" *Journal of Surgical Research* 149:84-93 (2008).
Bohl-Masters et al. "Effects of nitric oxide releasing poly(vinyl alcohol) hydrogel dressings on dermal wound healing in diabetic mice" *Wound Repair and Regeneration* 10(5):286-294 (2002).
Hetrick et al. "Anti-biofilm efficacy of nitric oxide-releasing silica nanoparticles" *Biomaterials* 30:2782-2789 (2009).
International Search Report and the Written Opinion of the International Searching Authority corresponding to International Patent Application No. PCT/US2014/019536; dated Jul. 28, 2014.
Non-final Office Action corresponding to U.S. Appl. No. 14/191,958 (20 pages) (dated Oct. 7, 2015).
Office Action corresponding to related Chinese Patent Application No. 201480023840.8 (6 pages) (dated Aug. 16, 2018).
Examination Report corresponding to related European Patent Application No. 14756266.4 (5 pages) (dated Apr. 16, 2018).
Office Action corresponding to related Japanese Patent Application No. 2015-560366 (9 pages) (dated May 18, 2018).
Third Party Submission of Information and English Translation of the Abstract of Reasons for Submission corresponding to Japanese Patent Application No. 2015-560366 (5 pages) (dated Sep. 30, 2018).

* cited by examiner

TOPICAL COMPOSITIONS AND METHODS OF USING THE SAME

RELATED APPLICATIONS

This application is a 35 U.S.C. § 371 national stage application of International Application No. PCT/US2014/019536, filed on Feb. 28, 2014, which claims the benefit of U.S. Provisional Patent Application Ser. No. 61/770,615, filed Feb. 28, 2013, the disclosures of which are hereby incorporated by reference herein in their entirety.

FIELD

The present invention relates generally to compositions and methods of using the same.

BACKGROUND

Skin disorders may be topically treated with various pharmaceutical compositions.

The present invention addresses previous shortcomings in the art by providing topical compositions and methods of using the topical compositions.

SUMMARY

A first aspect of the present invention comprises a composition comprising a first viscosity increasing agent; at least one polyhydric alcohol; at least one buffering agent; at least one preservative; a second viscosity increasing agent; at least one organic solvent; at least one humectant; at least one active pharmaceutical ingredient; and water, wherein the composition is buffered to a pH of about 3 to about 11. In some embodiments, the pH of the composition may be about 3 to about 8. The composition may be cosmetically elegant.

A second aspect of the present invention comprises a composition comprising at least one polyhydric alcohol present in an amount of about 1% to about 30% by weight of the composition; at least one viscosity increasing agent present in an amount of about 0.1% to about 5% by weight of the composition; water present in an amount of about 70% to about 99% by weight of the composition; at least one buffering agent present in an amount of about 0.01% to about 2% by weight of the composition; and at least one preservative present in an amount of about 0.01% to about 1% by weight of the composition; wherein the composition is buffered to a pH of about 3 to about 8. The composition may be cosmetically elegant.

A further aspect of the present invention comprises a kit comprising a first composition comprising at least one polyhydric alcohol present in an amount of about 1% to about 30% by weight of the composition; at least one viscosity increasing agent present in an amount of about 0.1% to about 5% by weight of the composition; and water present in an amount of about 70% to about 99% by weight of the composition; and a second composition, wherein the second composition is anhydrous. The composition may be cosmetically elegant.

Another aspect of the present invention comprises a method of increasing the release of nitric oxide from an anhydrous topical gel containing a nitric oxide-releasing active pharmaceutical ingredient comprising: contacting the anhydrous topical gel with a first composition of the present invention (e.g., a hydrogel of the present invention) having a pH of about 4 to about 6 to provide a combined composition. In some embodiments, the combined composition may be applied to the skin of a subject. The combined composition may be cosmetically elegant. The nitric oxide-releasing active pharmaceutical ingredient may be a diazeniumdiolate modified macromolecule.

A further aspect of the present invention comprises a pharmaceutical composition comprising: an anhydrous topical gel comprising a moisture sensitive active pharmaceutical ingredient; and a first composition of the present invention (e.g., a hydrogel of the present invention) comprising means for reducing the pH of the anhydrous topical gel. The moisture sensitive active pharmaceutical ingredient may be a nitric oxide-releasing active pharmaceutical ingredient and the nitric oxide-releasing active pharmaceutical ingredient may be a diazeniumdiolate modified polysiloxane molecule.

Another aspect of the present invention comprises a method of treating acne vulgaris comprising topically applying a composition of the present invention to the skin of a subject. A therapeutically effective amount of the composition may be applied.

A further aspect of the present invention comprises a method of reducing inflammatory and/or noninflammatory lesions in a subject comprising topically applying a composition of the present invention to the skin of the subject. A therapeutically effective amount of the composition may be applied. In some embodiments, the composition may comprise a nitric oxide-releasing active pharmaceutical ingredient in an amount of about 0.5% to about 10% by weight of the composition. The composition may store and/or release nitric oxide in an amount of about 0.05% to about 3% by weight of the composition. The method may reduce inflammatory and/or noninflammatory lesions by about 10% or greater over a defined period of time compared to a subject who did not apply a composition of the present invention over the same time period. In some embodiments, the method may reduce inflammatory and/or noninflammatory lesions in a subject compared to a subject who did not apply a composition comprising a nitric oxide-releasing active pharmaceutical ingredient over the same period of time. The subject may see a reduction in inflammatory and/or noninflammatory lesions within 12 weeks or less, in some embodiments, within 8 weeks or less, and in further embodiments, within 4 weeks or less.

Another aspect of the present invention comprises a method of reducing *P. acnes* counts in a subject comprising topically applying a composition of the present invention to the skin of the subject. A therapeutically effective amount of the composition may be applied. In some embodiments, the composition may comprise a nitric oxide-releasing active pharmaceutical ingredient in an amount of about 0.5% to about 10% by weight of the composition. The composition may store and/or release nitric oxide in an amount of about 0.05% to about 3% by weight of composition. The method may reduce *P. acnes* counts by about 10% or greater over a defined period of time compared to a subject who did not apply a composition of the present invention over the same time period. In some embodiments, the method may reduce *P. acnes* counts in a subject compared to a subject who did not apply a composition comprising a nitric oxide-releasing active pharmaceutical ingredient over the same period of time. The subject may see a reduction in *P. acnes* counts within 12 weeks or less, in some embodiments, within 8 weeks or less, and in further embodiments, within 4 weeks or less.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

Figure 1:
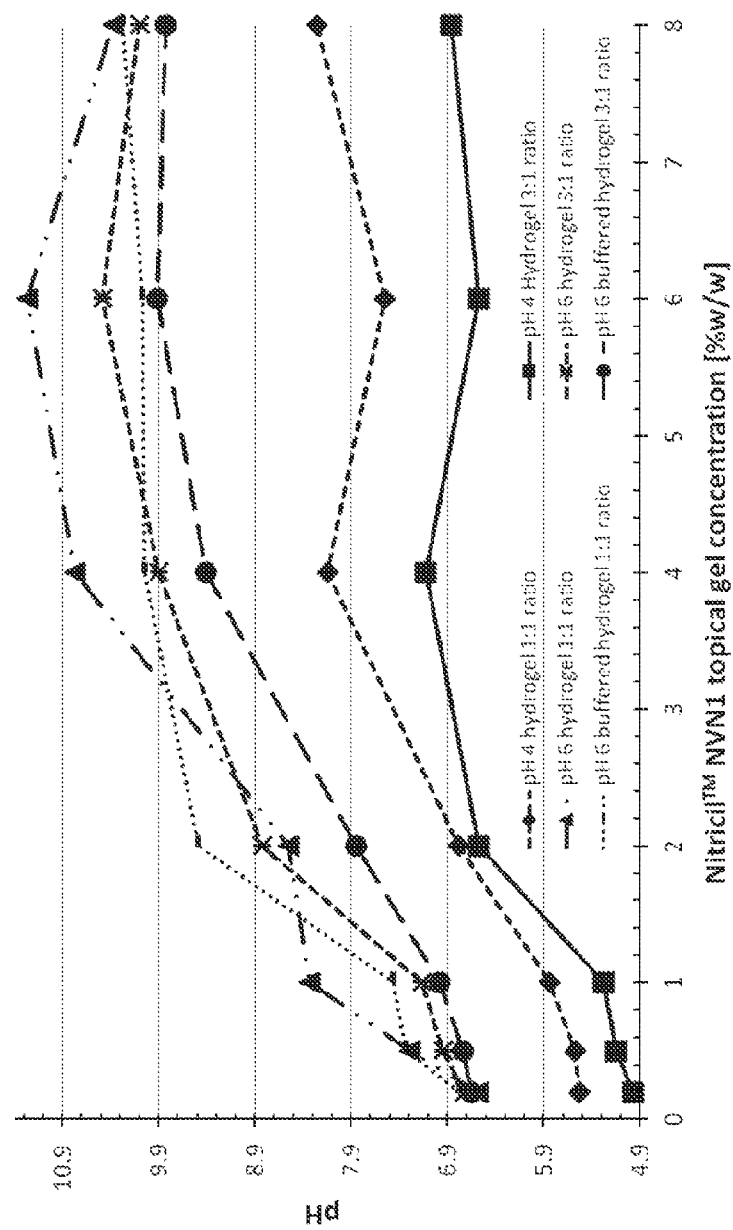
FIG. 1 shows a graph of the effects of Nitricil™ NVN1 Topical Gel strength, hydrogel pH, and hydrogel to Nitricil™ NVN1 Topical Gel ratio on the admixture pH.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (COPA 1976) (emphasis in the original); see also MPEP § 2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, is meant to include X as well as variations of ±20%, ±10%, ±5%, ±1%, ±0.5%, or even ±0.1% of X. A range provided herein for a measureable value may include any other range and/or individual value therein.

According to some embodiments of the present invention, provided herein are topical compositions. A composition of the present invention may comprise at least two parts. In some embodiments, a composition of the present invention comprises a first part comprising a first composition and a second part comprising a second composition. The second part of a composition of the present invention may comprise a nitric oxide-releasing active pharmaceutical ingredient (NO-releasing API). In some embodiments, a composition of the present invention may comprise a first part comprising a first composition that may be in the form of a hydrogel. "Hydrogel," as used herein, refers to a hydrophilic gel comprising a gel matrix and water. In some embodiments, a first composition of the present invention comprises at least one polyhydric alcohol, at least one viscosity increasing agent, and water.

In particular embodiments, a composition of the present invention comprises, consists essentially of, or consists of a first composition of the present invention and a second composition, wherein the first composition and the second composition are compatible with each other such that they may be mixed and/or combined together to provide the composition. A composition of the present invention may be referred to as a combined composition in some embodiments. In further aspects, the combined composition may be suitable for topical application to the skin of a subject.

Exemplary polyhydric alcohols that may be present in a first composition of the present invention include, but are not limited to, glycerol, propylene glycol, polyethylene glycol, polypropylene glycol, triethylene glycol, neopental glycols, butylene glycol, polyethylene glycol, sorbitol, arabitol, erythritol, HSH, isomalt, lactitol maltitol, mannitol, xylitol, threitol, ribitol, galactitol, fucitol, iditol, inositol, volemitol, and any combination thereof. In some embodiments, a first composition of the present invention comprises glycerol, such as, but not limited to, anhydrous glycerol.

A polyhydric alcohol may be present in a first composition of the present invention in an amount of about 1% to about 30% by weight of the first composition or any range and/or individual value therein, such as, but not limited to, about 1% to about 20%, about 1% to about 10%, or about 5% to about 15% by weight of the first composition. In certain embodiments, a polyhydric alcohol may be present in a first composition of the present invention in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the first composition or any range and/or individual value therein.

Exemplary viscosity increasing agents that may be present in a first composition of the present invention include, but are not limited to, a carboxypolymethylene; a polyacrylic polymer such as polyacrylic acid, a polyacrylate polymer, a cross-linked polyacrylate polymer, a cross-linked polyacrylic acid, and mixtures thereof; a cellulose ether such as hydroxyalkyl cellulose polymers such as hydroxypropyl methyl cellulose (HPMC), hydroxypropyl cellulose, hyrdoxyethyl cellulose, methyl cellulose, carboxymethyl cellulose, and mixtures thereof; a methacrylate; a polyvinylpyrollidone; cross-linked polyvinyl pyrrolidone; polyvinylpyrrolidone-vinyl acetate copolymer; polyvinylalcohol; polyethylene oxide; polyethylene glycol; polyvinylalkyl ether-maleic acid copolymer; a carboxy vinyl polymer; a polysaccharide; a gum such as sodium alginate, carrageenan, xantham gum, gum acacia, arabic gum, guar gum, pullulan, agar, chitin, chitosan, pectin, karaya gum, zein, hordein, gliadin, locust bean gum, tragacantha, and mixtures thereof; a protein such as collagen, whey protein isolate, casein, milk protein, soy protein, gelatin, and mixtures thereof; a starch such as maltodextrin, amylose, high amylase starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan, gluten, and mixtures thereof; bentonite; calcium stearate; ceratonia; colloidal silicon dioxide; dextrin; hypromellose; polycarbophil; kaolin; saponite; sorbitan esters; sucrose; sesame oil; tragacanth; potassium alginate; povidone; sodium starch glycolate; phospholipids; and any combination thereof.

In some embodiments, a first composition of the present invention comprises a carboxypolymethylene, such as, but not limited to, those commercially available from Lubrizol Corporation of Wickliffe, Ohio under the trade name Carbopol®. Exemplary Carbopol® polymers that may be present in a first composition of the present invention include, but are not limited to, Carbopol® 974P NF polymer, such as Type A, Type B and/or Type C Homopolymers; Carbopol® Ultrez 10, 20, 21 NF polymer; Carbopol® 971 P NF polymer; Carbopol® 980 Homopolymer Type C polymer, Carbopol® 980 NF polymer, Carpobol® 980P polymer, Carbopol® ETD 2020 NF polymer, Carbopol® 71 G NF polymer, Carbopol® 981P NF polymer, Carbopol® 970P NF polymer, Carbopol® 981P NF polymer, Carbopol® 5984P NF polymer, Carbopol® 934P NF polymer, Carbopol® 940P NF polymer, Carbopol® 941P NF polymer, Carbopol® 13242 NF polymer, Carbopol® AA-1 USP NF polymer, Carbopol® TR1 NF polymer, Carbopol® TR2 NF polymer, Lubrizol Aqua CC polymer and SF-2 polymer, and any combination thereof.

In some embodiments, a viscosity increasing agent present in a first composition of the present invention may be a polymer comprising acidic groups, such as, but not limited to, carboxylic acid groups. The acidic groups of the polymer may be partially neutralized in a first composition of the present invention. In certain embodiments, a viscosity increasing agent present in a first composition of the present invention may be a carboxypolymethylene. In some embodiments, a carboxypolymethylene present in a first composition of the present invention may be partially neutralized. A first composition of the present invention may comprise a carboxypolymethylene and have a pH of about 3 to about 7, about 3.5 to about 6.5, about 3.5 to about 6, or about 4 to about 6. In certain embodiments, a first composition of the present invention may comprise a carboxypolymethylene and have a pH of about 3, 3.5, 4, 4.5, 5, 5.5, 6, 6.5, or 7.

A viscosity increasing agent may be present in a first composition of the present invention. In some embodiments, a composition of the present invention may comprise at least two viscosity increasing agents that may be the same or different. In some embodiments, a first viscosity increasing agent may be present in a first composition of the present invention in an amount of about 0.01% to about 5% by weight of the first composition or any range and/or individual value therein, such as, but not limited to, about 0.05% to about 3% or about 0.1% to about 1.5% by weight of the first composition. In certain embodiments, a first viscosity increasing agent is present in a first composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the first composition or any range and/or individual value therein.

Water may be present in a first composition of the present invention in an amount of about 70% to about 99% by weight of the first composition or any range and/or individual value therein, such as, but not limited to, about 75% to about 95% or about 80% to about 90% by weight of the first composition. In certain embodiments, water is present in a first composition of the present invention in an amount of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the first composition or any range and/or individual value therein.

In some embodiments, a first composition of the present invention comprises, consists essentially of, or consists of at least one polyhydric alcohol present in an amount of about 1% to about 30% by weight of the first composition, at least one viscosity increasing agent present in an amount of about 0.1% to about 5% by weight of the first composition, and water present in an amount of about 70% to about 99% by weight of the first composition. In certain embodiments, the viscosity increasing agent may be a carboxypolymethylene. The first composition may be a hydrogel.

A first composition of the present invention may comprise a preservative. A preservative may be present in a first composition of the present invention in an amount of about 0.01% to about 1% by weight of the first composition or any range and/or individual value therein, such as, but not limited to, about 0.01% to about 0.1%, about 0.05% to about 1%, or about 0.1% to about 1% by weight of the first composition. In certain embodiments, a preservative is present in a first composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the first composition or any range and/or individual value therein. Exemplary preservatives that may be present in a first composition of the present invention include, but are not limited to, sorbic acid, benzoic acid, methyl-paraben, propyl-paraben, methyl chloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A first composition of the present invention may comprise a neutralizing agent. A neutralizing agent may be present in a first composition of the present invention in an amount sufficient to provide a desired pH, such as, but not limited to, a pH of about 3 to about 11, or any range and/or individual value therein, such as, but not limited to, about 3 to about 8, about 4 to about 7, or about 6 to about 7, or about 6 to 11.

In some embodiments, a neutralizing agent may be present in a first composition in an amount sufficient to provide the first composition with a pH between about 3 to about 8.

In certain embodiments, a neutralizing agent may be present in a first composition of the present invention in an amount sufficient to provide a composition of the present invention with a desired pH upon combination of the first composition and a second part (e.g., a second composition) and/or upon administration of the first composition and/or the composition comprising the first composition and the second part to the skin of a subject. A neutralizing agent may be present in a first composition of the present invention in an amount sufficient to provide a composition of the present invention (e.g., a composition comprising the first composition and a second composition) with a desired pH, such as, but not limited to, a pH of about 3 to about 11, or any range and/or individual value therein.

The pH of a composition of the present invention may be determined once a steady state pH is achieved after contact, combination, and/or mixing of the first part and second part of the composition of the present invention. Alternatively or in addition, the pH of a composition of the present invention may be determined after a defined period of time, such as, but not limited to, after about 5, 10, 15, 20, 25, 30, 35, 40, 45, 50, 55, 60 minutes or more. The pH of a composition of the present invention may be measured in vitro after contact, combination, and/or mixing of the first part and second part of a composition of the present invention. Alternatively or in addition, the pH of a composition of the present invention may be measured after administration to a subject, such as, for example, a skin surface pH may be measured after administration of a composition of the present invention to the skin of a subject.

In some embodiments, a neutralizing agent adjusts the pH of the first composition and/or composition of the present invention. In certain embodiments of the present invention, a neutralizing agent is present in a first composition of the present invention in an amount sufficient for the first composition to have a pH of about 3, 3.5, 4, 4.5, 5, 5.5, 6, 6.5, 7, 7.5, or 8 or any range and/or individual value therein. In some embodiments of the present invention, a neutralizing agent is present in a composition of the present invention in an amount sufficient for the composition to have a pH of about 3, 3.5, 4, 4.5, 5, 5.5, 6, 6.5, 7, 7.5, 8, 8.5, 9, 9.5, 10, 10.5, or 11, or any range and/or individual value therein.

Exemplary neutralizing agents that may be present in a first composition of the present invention include, but are not limited to, bases such as sodium hydroxide, potassium hydroxide, and mixtures thereof; acids such as hydrochloric acid, citric acid, lactic acid, glycolic acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof.

A neutralizing agent may be present in a first composition of the present invention in an amount of about 0.01% to about 1% by weight of the first composition or any range and/or individual value therein, such as, but not limited to, about 0.01% to about 0.1%, about 0.05% to about 1%, or about 0.1% to about 1% by weight of the first composition. In certain embodiments, a neutralizing agent may be present in a first composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the first composition or any range and/or individual value therein.

A first composition of the present invention may be unbuffered or buffered. In some embodiments, a first composition of the present invention may be unbuffered. In other embodiments, a first composition of the present invention may be buffered. Exemplary buffers that may be present in first composition of the present invention include, but are not limited to, acetic acid/acetate buffers; hydrochloric acid/citrate buffers; vitro-phosphate buffers; phosphate buffers; citric acid/citrate buffers; lactic acid buffers; tartaric acid buffers; malic acid buffers; glycine/HCl buffers; saline buffers such as phosphate buffered saline (PBS), Tris-buffered saline (TBS), Tris-HCl, NaCl, Tween buffered saline (TNT), phosphate buffered saline, Triton X-100 (PBT) and mixtures thereof; cacodylate buffers; barbital buffers; tris buffers; and any combination thereof.

In certain embodiments, a first composition of the present invention may comprise a buffering agent. Exemplary buffering agents include, but are not limited to, citric acid, acetic acid, lactic acid, boric acid, succinic acid, malic acid, and any combination thereof. A buffering agent may be present in a first composition of the present invention in an amount of about 0.01% to about 2% by weight of the first composition or any range and/or individual value therein, such as, but not limited to, about 0.01% to about 0.1%, about 0.05% to about 1%, about 0.1% to about 0.5%, or about 0.1% to about 2% by weight of the first composition. In certain embodiments, a buffering agent is present in a first composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the first composition or any range and/or individual value therein.

In some embodiments, a buffer and/or buffering agent is present in a first composition of the present invention in an amount sufficient for the first composition to have a pH of about 3 to about 8 or any range and/or individual value therein, such as, but not limited to, about 3 to about 6, about 3 to about 5, about 4 to about 7, about 5 to about 7, or about 6 to about 7. In certain embodiments of the present invention, a buffer and/or buffering agent may be present in a first composition of the present invention in an amount sufficient for the first composition to have a pH of about 3, 3.5, 4, 4.5, 5, 5.5, 6, 6.5, 7, 7.5, or 8, or any range and/or individual value therein.

In some embodiments, a buffer and/or buffering agent may be present in a first composition of the present invention in an amount sufficient to provide a desired pH for a composition of the present invention comprising the first composition and a second part (e.g., a second composition). For example, a composition of the present invention may comprise a second composition and a first composition comprising a buffer and/or buffering agent, wherein the buffer and/or buffering agent is present in an amount sufficient to provide the composition with a pH of about 3 to about 11, such as, but not limited to, about 3 to about 8, about 7 to about 11, about 8 to about 10, about 3 to about 5, about 4 to about 7, about 5 to about 7, or about 6 to about 7. In certain embodiments of the present invention, a buffer and/or buffering agent may be present in a first composition of the present invention in an amount sufficient for the composition to have a pH of about 3, 3.5, 4, 4.5, 5, 5.5, 6, 6.5, 7, 7.5, 8, 8.5, 9, 9.5, 10, 10.5, or 11, or any range and/or individual value therein. In some embodiments, the buffer and/or buffering agent may be present in a first composition of the present invention in an amount sufficient to provide a desired pH upon administration of a composition of the present invention comprising the first composition and a second part to the skin of a subject.

In some embodiments, a buffer, buffering agent, and/or neutralizing agent may be present in a first composition of the present invention in an amount sufficient to provide a composition of the present invention and/or a first composition of the present invention with a desired pH.

In certain embodiments, a first composition of the present invention comprises at least one polyhydric alcohol present in an amount of about 1% to about 30% by weight of the first composition, at least one viscosity increasing agent present in an amount of about 0.1% to about 5% by weight of the first composition, water present in an amount of about 70% to about 99% by weight of the first composition, and at least one preservative in an amount of about 0.01% to about 1% by weight of the first composition. The first composition may be buffered to have a pH in a range of about 3 to about 8, about 3 to about 6, or about 6 to about 8. The first composition may be a hydrogel.

In some embodiments, a first composition of the present invention may comprise, consist essentially of, or consist of a polyhydric alcohol in an amount of about 1% to about 30% by weight of the first composition, a viscosity increasing agent in an amount of about 0.01% to about 5% by weight of the first composition, water in an amount of about 70% to about 99% by weight of the first composition, optionally a buffering agent in an amount of about 0.001% to about 2% by weight of the first composition, optionally a preservative in an amount of about 0.001% to about 1% by weight of the first composition, and optionally a neutralizing agent in an amount of about 0.001% to about 1% by weight of the first composition. The first composition may have a pH in a range of about 3 to about 5 or about 5 to about 7. In certain embodiments, the viscosity increasing agent present in the first composition may be a carboxypolymethylene. In some embodiments, the first composition may be cosmetically elegant. The first composition may be a hydrogel.

As those skilled in the art will recognize in light of the present disclosure, the properties of a first composition of the present invention may confer and/or provide the same and/or similar properties to a composition of the present invention. For example, in some embodiments, a first composition of the present invention may comprise a preservative that is present in an amount sufficient to provide antimicrobial activity to the first composition and/or a composition of the present invention. Thus, in some embodiments, a first composition and/or a composition of the present invention may be antimicrobial.

A composition and/or first composition of the present invention may have a viscosity in a range of about 5,000 cP to about 25,000 cP or any range and/or individual value therein, such as, but not limited to, about 5,000 cP to about 20,000 cP or about 7,000 cP to about 15,000 cP. In certain embodiments, a composition and/or first composition of the present invention may have a viscosity of about 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, or 25,000 cP or any range and/or individual value therein.

In some embodiments, a composition of the present invention may comprise a first composition of the present invention that has a viscosity that allows for mixing and/or combination with a second part of the composition. For example, a first composition of the present invention may have a viscosity suitable and/or sufficient for mixing and/or combination with a second part of a composition of the present invention in a person's hand and/or on a subject's skin. A first composition with too low of a viscosity may run off the skin of a subject prior to mixing and/or combination. A first composition with too high a viscosity may be difficult to mix with the second part of a composition of the present invention and/or difficult to spread and/or apply the combined composition on the skin of a subject.

A composition and/or first composition of the present invention may comprise an active pharmaceutical ingredient (API). Any suitable API or combinations of APIs may be included in a composition and/or first composition of the present invention. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents, and any combination thereof. Exemplary APIs include, but are not limited to, those described in International Application Publication No. WO 2013/006608, which is incorporated herein by reference in its entirety.

In some embodiments, a first composition of the present invention may not comprise an API. In certain embodiments, a first composition of the present invention does not contain a nitric oxide (NO) releasing API. In some embodiments, a first composition of the present invention may comprise at least one API, but the first composition may not comprise an NO-releasing API.

In certain embodiments, a first composition of the present invention may comprise an API. The API in the first composition may be a moisture sensitive API. In some embodiments, a first composition of the present invention comprises an API (e.g., a moisture sensitive API) and the second part and/or composition of a composition of the present invention comprises a second API, wherein the API in the first composition and the second API in the second part and/or composition may not be chemically compatible and/or stable in the composition of the present invention. For example, the API in the first composition and the second API in the second part and/or composition may not be chemically compatible and/or stable when stored together in a composition of the present invention.

A first composition of the present invention may be suitable for use and/or combination with one or more, such as, but not limited to, 2, 3, 4, or more, compositions that may be the same and/or different. In some embodiments, a first composition of the present invention may be suitable for use and/or combination with one or more pharmaceutical compositions. A first composition of the present invention may be used as a drug delivery system and/or a drug release system. For example, a first composition of the present invention may be configured to modulate the release of an API in a second composition upon contact of the first composition of the present invention (e.g., a hydrogel of the present invention) and a second composition. Alternatively or in addition, a first composition of the present invention may be configured to modulate the pH of a second composition upon contact of the first composition of the present invention (e.g., a hydrogel of the present invention) and the second composition. In some embodiments, a first composition of the present invention may be configured to modulate the pH of a second composition comprising a nitric oxide (NO) releasing API and/or the release of nitric oxide from an NO releasing API in a second composition.

"Modulate," "modulating," "modulation," and grammatical variations thereof as used herein refer to an increase or reduction in the pH of a second composition and/or the release of an API in a second composition compared to the pH of the second composition and/or the release of the API in the second composition in the absence of a first composition of the present invention. As used herein, the terms "increase," "increases," "increased," "increasing" and similar terms indicate an elevation in the pH and/or release of at least about 5%, 10%, 25%, 50%, 75%, 100%, 150%, 200%, 300%, 400%, 500% or more compared to the pH and/or release in the absence of a first composition of the present invention. As used herein, the terms "reduce," "reduces," "reduced," "reduction" and similar terms refer to a decrease in the pH and/or release of at least about 5%, 10%, 25%, 35%, 50%, 75%, 80%, 85%, 90%, 95%, 97% or more compared to the pH and/or release in the absence of a first composition of the present invention.

"Contact," as used herein in reference to a first composition of the present invention (e.g., a hydrogel of the present invention) and a second part and/or composition, refers to direct and/or indirect exposure of at least one component in the first composition to the second part and/or composition. Contact of the first composition and second part and/or composition may be accomplished by any means, such as, but not limited to, by mixing, stirring, blending, dispersing, milling, homogenizing, combining, applying to same area or region, and the like, and in some embodiments may optionally form a combined composition of the present invention. For example, a first composition may come into direct contact with a second composition, such as, but not limited to, by mixing and/or combining the first composition and second composition to form a combined composition of the present invention prior to, during, and/or after topical application to a subject. Direct contact of a first composition and second composition may occur by applying one or more layers of the second composition onto a subject and then applying one or more layers of the first composition onto a subject or vice versa to form a combined composition of the present invention. Indirect contact may occur by applying a second composition onto a subject and then applying a first composition onto a subject through a substrate, such as, but not limited to, a cloth, bandage, gauze, and the like, or vice versa to optionally form a combined composition of the present invention.

According to some embodiments of the present invention, upon contact of a first composition of the present invention and a second composition, a first composition of the present invention may be configured to modulate the release of an API present in the second composition, such as, but not limited to, an NO releasing API. In some embodiments, water and/or a proton(s) present in a first composition of the present invention may contact a second composition to modulate the release of an API present in the second composition, such as, but not limited to, an NO releasing API. Alternatively or in addition, in some embodiments, contact of a first composition of the present invention with a second composition may modulate the pH of the second composition, thereby modulating the release of an API present in the second composition, such as, but not limited to, an NO releasing API. In some embodiments, a first composition of the present invention is configured to supply water and/or a proton(s) to a second composition and/or configured to modulate the pH of a second composition.

Figure 12:
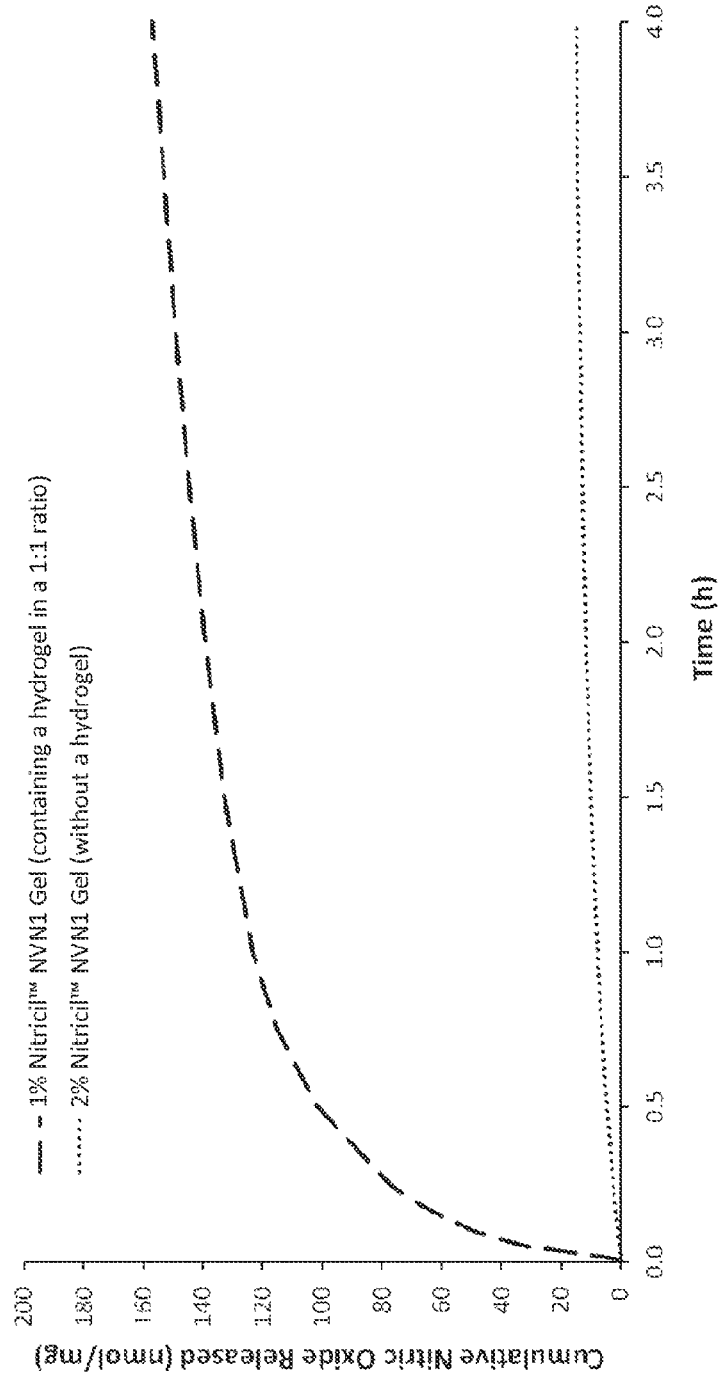
FIG. 12 shows a graph of the cumulative nitric oxide release for a 2% Nitricil™ NVN1 Gel without a hydrogel and a 1% Nitricil™ NVN1 Gel containing a hydrogel (the gel to hydrogel ratio was 1:1).

It was surprisingly discovered by the inventors of the present invention that embodiments of the present invention could significantly increase the amount of nitric oxide released from a composition comprising an NO-releasing API and/or provide a continuous release of nitric oxide from a composition comprising an NO-releasing API. For example, this can be seen in FIG. 12, which compares a composition without a first composition of the present invention (i.e., the 2% Nitricil™ NVN1 Gel) and a composition of the present invention comprising a first composition of the present invention (i.e., the 1% Nitricil™ NVN1 Gel). The 2% Nitricil™ NVN1 Gel and the part of 1% Nitricil™ NVN1 Gel with the NO-releasing API contained the same amount of the NO-releasing API. FIG. 12 demonstrates that the 1% Nitricil™ NVN1 Gel had a significantly higher amount of nitric oxide released and also provided for a continuous release of nitric oxide over a period of time compared to the 2% Nitricil™ NVN1 Gel.

While not wishing to be bound to any particular theory, it is believed that a composition of the present invention comprising a first composition of the present invention and a NO-releasing API may provide a proton donating system that may provide for a high release of nitric oxide from the composition and/or a continuous release of nitric oxide from the composition. The proton donating system, while not wishing to be bound to any particular theory, may be an acid that may be formed by a composition of the present invention (e.g., a composition comprising a first composition of the present invention and a second composition as described herein) and/or a first composition of the present invention (e.g., a hydrogel of the present invention). A composition of the present invention may provide and/or allow for a proton to be in close proximity to an NO-donor in an NO-releasing API to thereby allow for the release of nitric oxide. A composition of the present invention may provide and/or allow for a proton to be in proximity of an NO-donor for an extended period of time to provide a continuous release of NO for about 1 or more hours, such as, but not limited to, 2, 3, 4, 5, 6, 7, 8, 9, 10, 11, 12, or more hours.

The proton donating system may be provided by a first composition of the present invention. For example, a proton donating system may be provided by a first composition of the present invention comprising an acidic polymer, such as, but not limited to, carboxypolymethylene, wherein the acidic polymer is partially neutralized and the first composition has a pH of about 3 to about 8 or any range therein, such as, but not limited to, about 3 to about 6, about 3 to about 6, or about 5 to about 7. While not wishing to be bound to any particular theory, the partially neutralized acidic polymer may provide the first composition with a polymeric gel matrix having a coiled structure. The coiled structure of the polymeric gel matrix may provide and/or donate protons when the protons are in proximity to an NO donor in a composition of the present invention and the coiled structure may protect some protons (e.g., interior protons) from reacting with an NO donor in the composition. As the polymeric gel matrix uncoils (e.g., as the pH of the composition becomes more basic and/or the polymeric gel matrix becomes neutralized), additional protons (e.g., the protected protons) may be in proximity to a NO donor, and this may provide for the release of nitric oxide from the composition over a longer period of time and/or for a higher amount of nitric oxide released from the composition.

In particular embodiments, a first composition of the present invention modulates the pH of a second composition such that when the first and second compositions are contacted and/or applied to the skin of a subject, the pH of the second composition and/or combined composition (i.e., a composition of the present invention) is less that about 11, in some embodiments, less than about 10, in certain embodiments, less than about 8.5, in further embodiments, less than about 7, and in still further embodiments, between about 6 and about 8.

In some embodiments, the pH of a combined composition of the present invention changes upon application of the combined composition to the skin of a subject. In particular embodiments, the pH of a combined composition of the present invention is decreased by the buffering capacity of the skin upon application of the combined composition to the skin of a subject. In some embodiments, the pH of a combined composition of the present invention after application of the combined composition to the skin of a subject is less than the pH of the second composition applied to the skin without the first composition. In embodiments where the release kinetics of the API in a second composition varies with pH, the buffering capacity of the skin may be utilized to modulate release while improving stability of the combined composition after combination and before application. Thus, for example, the pH of a second composition that includes a nitric oxide-releasing macromolecule may be greater than 10 before mixing, 9 after mixing and 8 after application to the skin. With each decrease in pH, the release of nitric oxide from the macromolecule may be increased. Accordingly, taking advantage of the changing pH and buffering capacity of the skin may allow for increased working time (e.g., mixing and application time) for a combined composition of the present invention.

In some embodiments, a composition of the present invention may comprise a second composition and the second composition may be an anhydrous composition. "Anhydrous," as used herein, means that there is no direct addition of water to the second composition when it is being prepared. However, those skilled in the art will recognize that water may be physically and/or chemically absorbed by the second composition and/or by one or more ingredients in the second composition at any time during the preparation, storage, and/or use of the second composition (i.e., indirect addition of water to the second composition). In some embodiments, the term "anhydrous" means that the second composition has a water content of less than 5% by weight of the second composition or any range and/or individual value therein. A second composition may have a water content of less than 5, 4.5, 4, 3.5, 3, 2.5, 2, 1.5, 1, or 0.5%, or any range therein, by weight of the second composition. Water content may be measured by methods known to those of skill in the art, such as, but not limited to, Karl Fischer titration. In certain embodiments, upon contact with a second composition, a composition of the present invention adds water to the second composition and/or the second composition absorbs water from a composition of the present invention.

Exemplary second compositions that may be used and/or placed in contact with a first composition of the present invention include, but are not limited to, those described in International Application Publication No. WO 2013/006608, which is incorporated herein by reference in its entirety. An exemplary second composition that may be used and/or placed in contact with a first composition of the present invention to form a composition of the present invention (e.g., a combined composition of the present invention) may comprise an anhydrous composition comprising at least one viscosity increasing agent present in the second composition in an amount of about 0.5% to about 30% by weight of the second composition, at least one organic solvent present in the second composition in an amount of about 50% to about 90 by weight of the second composition, and at least one humectant present in the second composition in an amount of about 2% to about 20% by weight of the second composition. The second composition may further comprise at least one water repelling agent, also referred to as a water repellant. In certain embodiments, the second composition may comprise a composition as set forth in Table 11.

Exemplary viscosity increasing agents for the second composition include, but are not limited to, co-polymers of carboxymethylcellulose and acrylic acid, N-vinylpyrrolidone, polyalkylene glycols (e.g., poly(ethylene glycol)), polyalkylene oxides (e.g., polyethylene oxide), polyvinyl alcohols, polyvinylpyrrolidone, polysiloxanes, poly(vinyl acetates), cellulose, derivatized celluloses, alginates, copolymers thereof and blends thereof. A specific example of a viscosity agent for the second composition is a hydroxypropylcellulose, such as Klucel® hydroxypropylcellulose (e.g., Klucel® MF Pharm grade). A viscosity increasing agent may be present in the second composition in an amount of about 0.1% to about 30% by weight of the second composition or any range and/or individual value therein, such as, but not limited to, about 0.5% to about 20%, about 1% to about 10%, or about 1% to about 5% by weight of the second composition. In certain embodiments, a viscosity increasing agent may be present in the second composition in an amount of about 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the second composition or any range and/or individual value therein.

Exemplary organic solvents for the second composition include, but are not limited to, acetone, methyl alcohol, ethanol, isopropanol, butyl alcohol, ethyl acetate, dimethyl isosorbide, propylene glycol, glycerol, ethylene glycol, polyethylene glycol, diethylene glycol monoethyl ether or mixtures thereof. In some embodiments of the present invention, the organic solvent in the second composition may be ethanol and/or isopropyl alcohol. An organic solvent may be present in the second composition in an amount of about 50% to about 90% by weight of the second composition or any range and/or individual value therein, such as, but not limited to, about 60% to about 90%, about 70% to about 90%, or about 75% to about 85% by weight of the second composition. In certain embodiments, an organic solvent may be present in the second composition in an amount of about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% by weight of the second composition or any range and/or individual value therein.

Exemplary humectants for the second composition include, but are not limited to, glycols, such as diethylene glycol monoethyl ether; glycerols; sugar polyols, such as sorbitol, xylitol and maltitol; polyols such as polydextroses; quillaia, urea, and blends thereof. In some embodiments, the humectant in the second composition may comprise an alkylene glycol, such as, for example, hexylene glycol. A humectant may be present in the second composition in an amount of about 2% to about 20% by weight of the second composition or any range and/or individual value therein, such as, but not limited to, about 2% to about 15%, about 5% to about 15%, or about 15% to about 20%© by weight of the second composition. In certain embodiments, a humectant may be present in the second composition in an amount of about 2%, 3%, 4%, 5%, 6%, 7%, 8%, 9%, 10%, 11%, 12%, 13%, 14%, 15%, 16%, 17%, 18%, 19%, or 20% by weight of the second composition or any range and/or individual value therein.

Exemplary water repellants for the second composition include, but are not limited to, silicones, such as cyclomethicone, dimethicone, simethicone, C26-28 alkyl dimethicone, C26-28 alkyl methicone, polyphenylsisquioxane, trimethylsiloxysilicate and crosspolymers of cyclopentasiloxane and dimethicone/vinyltrimethylsiloxysilicate, and blends thereof. In some embodiments, a second composition may comprise cyclomethicone. A water repellant may be present in the second composition in an amount of about 0.5% to about 15% by weight of the second composition or any range and/or individual value therein, such as, but not limited to, about 0.5% to about 10%, about 1% to about 5%, or about 2% to about 5% by weight of the second composition. In certain embodiments, a water repellant may be present in the second composition in an amount of about 0.5%, 1%, 2%, 3%, 4%, 5%, 6%, 7%, 8%, 9%, 10%, 11%, 12%, 13%, 14%, or 15% by weight of the second composition or any range and/or individual value therein.

Accordingly, a composition of the present invention may comprise at least one polyhydric alcohol, a first viscosity increasing agent, at least one preservative, at least one buffering agent, water, a second viscosity increasing agent, at least one organic solvent, at least one humectant, and optionally a water repelling agent.

A composition of the present invention (e.g., a first composition of the present invention and a second composition) may be buffered to a pH of about 3 to about 11, such as, but not limited to, about 3 to about 9.5 or about 3 to about 8. In some embodiments, a composition of the present invention may have a pH of 9.5 or greater. In certain embodiments, the composition of the present invention comprises at least one API, such as, but not limited to, a nitric oxide-releasing active pharmaceutical ingredient. In some embodiments, a composition of the present invention may comprise a second composition comprising a nitric oxide-releasing active pharmaceutical ingredient.

In some embodiments, a composition of the present invention comprises a second composition, wherein the second composition comprises a moisture sensitive API. The second composition may stably store the moisture sensitive API. In some embodiments, the moisture sensitive API may comprise an NO-releasing API, such as, but not limited to a diazeniumdiolate modified macromolecule.

"Nitric oxide releasing active pharmaceutical ingredient" and "NO releasing API," as used herein, refer to a compound or other composition that provides nitric oxide to the skin of a subject, but is not gaseous nitric oxide. In some embodiments, the NO releasing API includes a nitric oxide-releasing compound, hereinafter referred to as a "NO-releasing compound." An NO-releasing compound includes at least one NO donor, which is a functional group that may release nitric oxide under certain conditions. In some embodiments, the at least one NO donor of an NO-releasing compound releases NO when in contact with a composition of the present invention. In certain embodiments, a composition of the present invention modulates the amount of NO released from an NO-releasing compound and/or the rate of NO released from an NO-releasing compound. In some embodiments, a composition of the present invention increases the amount of NO released from an NO-releasing compound and/or the rate of NO released from an NO-releasing compound.

Any suitable NO-releasing compound may be used. In some embodiments, the NO-releasing compound includes a small molecule compound that includes an NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 μm and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in a second composition as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Application Publication No. 2009/0214618, the disclosure of which is incorporated by reference herein in its entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the present invention, a nitric oxide-releasing active pharmaceutical ingredient may include NO-loaded precipitated silica. The NO-loaded precipitated silica may be formed from nitric oxide donor modified silane monomers into a co-condensed siloxane network. In one embodiment of the present invention, the nitric oxide donor may be an N-diazeniumdiolate. In some embodiments of the present invention, the nitric oxide-releasing active pharmaceutical ingredient may comprise, consist essentially of, or consist of a co-condensed siloxane network comprising a diazeniumdiolate (e.g., a N-diazeniumdiolate).

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors. In some embodiments of the present invention, the nitric oxide-releasing active pharmaceutical ingredient may comprise, consist essentially of, or consist of a co-condensed silica network synthesized from the condensation of a silane mixture comprising an alkoxysilane and at least one aminoalkoxysilane having an amine substituted by a diazeniumdiolate (e.g., a N-diazeniumdiolate).

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: R"—(NH—R')n-Si(OR)3, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl) phenethyltrimethoxysilane (AEMP3); [3-(methylamino) propyl]trimethoxysilane (MAP3); N-butylaminopropyltrimethoxysilane(n-BAP3); t-butylaminopropyltrimethoxysilane(t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: NH[R'—Si(OR)3]2, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl) propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R"—N(NONO—X+)—R—Si(OR)3, wherein R is alkyl, R' is alkylene or aralkylene, R" is alkyl or alkylamine, and X+ is a cation selected from the group consisting of Na+, K+ and Li+.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of R"'—N(NONO—X+)—R'—Si(OR)3, wherein: R is alkyl, R' is alkylene or aralkylene, R" is alkyl or alkylamine, and X+ is a cation selected from the group consisting of Na+ and K+.

In certain embodiments, the NO-releasing API may comprise a co-condensed silica network comprising diazeniumdiolated aminoethylaminopropyl trimethoxy silane (AEAP3) and tetra methyl orthosilicate (TMOS) and/or a co-condensed silica network comprising diazeniumdiolated aminoethylaminopropyl trimethoxy silane (AEAP3) and tetraethyl orthosilicate (TEOS). In some embodiments, the NO-releasing API may comprise a co-condensed silica network comprising diazeniumdiolated methylaminopropyl trimethoxysilane (MAP3) and tetra methyl orthosilicate (TMOS) and/or a co-condensed silica network comprising diazeniumdiolated methylaminopropyl trimethoxysilane (MAP3) and tetraethyl orthosilicate (TEOS).

In some embodiments of the invention, the particle size of a NO-releasing API may be in a range of about 20 nm to about 20 μm or any range therein, such as, but not limited to, about 100 nm to about 20 μm or about 1 μm to about 20 μm. The particle size may be tailored to minimize or prevent toxicity and/or penetration through the epidermis (or compromised dermis) and into the blood vessels. In particular embodiments, the particle size is distributed around a mean particle size of less than 20 µm, or any range therein, and the size may allow the particle to enter a follicle. In some embodiments, a NO-releasing API may have a particle size that is distributed around a mean particle size of about 20, 19, 18, 17, 16, 15, 14, 13, 12, 11, 10, 9, 8, 7, 6, 5, 4, 3, 2, or 1 µm. In further embodiments, a NO-releasing API may have a particle size that is distributed around a mean particle size of less than 10 µm, or any range therein, such as, but not limited to about 2 µm to about 10 µm or about 4 µm to about 8 µm. In other embodiments, the particle size may be distributed around a mean particle size of greater than 20 µm, or any range therein, and the size may prevent the particle from entering the follicle. In still further embodiments, a mixture of particles with mean particle sizes distributed around two or more mean particle sizes may be provided. A NO-releasing API may be micronized (e.g., ball and/or jet milled). Methods for providing a desired particle size and/or micronization include, but are not limited to, those described in U.S. Patent Application Publication No. 2013/0310533, which is incorporated herein by reference in its entirety.

A nitric oxide-releasing active pharmaceutical ingredient may be present in a composition of the present invention in an amount of about 0.5% to about 10% by weight of the composition, such as, but not limited to, about 1% to about 8% or about 2% to about 6%. In certain embodiments, a nitric oxide-releasing active pharmaceutical ingredient may be present in a composition of the present invention in an amount of about 0.5%, 1%, 2%, 3%, 4%, 5%, 6%, 7%, 8%, 9%, or 10%. A composition of the present invention may comprise a nitric oxide-releasing active pharmaceutical composition and may store and/or release nitric oxide in an amount of about 0.05% to about 3% by weight of composition, such as, but not limited to, about 0.15% to about 2%, about 0.15% to about 1%, about 0.3% to about 1.2%. In certain embodiments, a composition of the present invention may comprise a nitric oxide-releasing active pharmaceutical and may store and/or release nitric oxide in an amount of about 0.15%, 0.3%, 0.6%, 0.9%, 1%, 1.2%, 1.5%, 1.75%, 2%, 2.25%, 2.5%, 2.75%, or 3%.

In some embodiments, a first composition of the present invention may increase the amount of NO released from a composition (e.g., a second composition comprising a NO-releasing API) compared to the amount of NO released from the composition in the absence of a first composition of the present invention over the same period of time. In certain embodiments, a first composition of the present invention may increase the amount of NO released from a composition of the present invention comprising the first composition and a NO-releasing API by at least about 10%, 20%, 30%, 40%, 50%, 60%, 70%, 80%, 90, or more, or any range and/or individual value therein compared to the amount of NO released in the absence of a first composition of the present invention over the same period of time. Therefore, a composition of the present invention (e.g., a composition comprising a first composition of the present invention and a second composition comprising a NO-releasing API) may release about 1.5 to about 100 times more NO than the amount of NO released in the absence of a first composition of the present invention (e.g., the second composition alone) over the same period of time or any range and/or individual value therein, such as, but not limited to between about 2 and 10 times more NO or between about 5 and about 50 times more NO.

Figure 7:
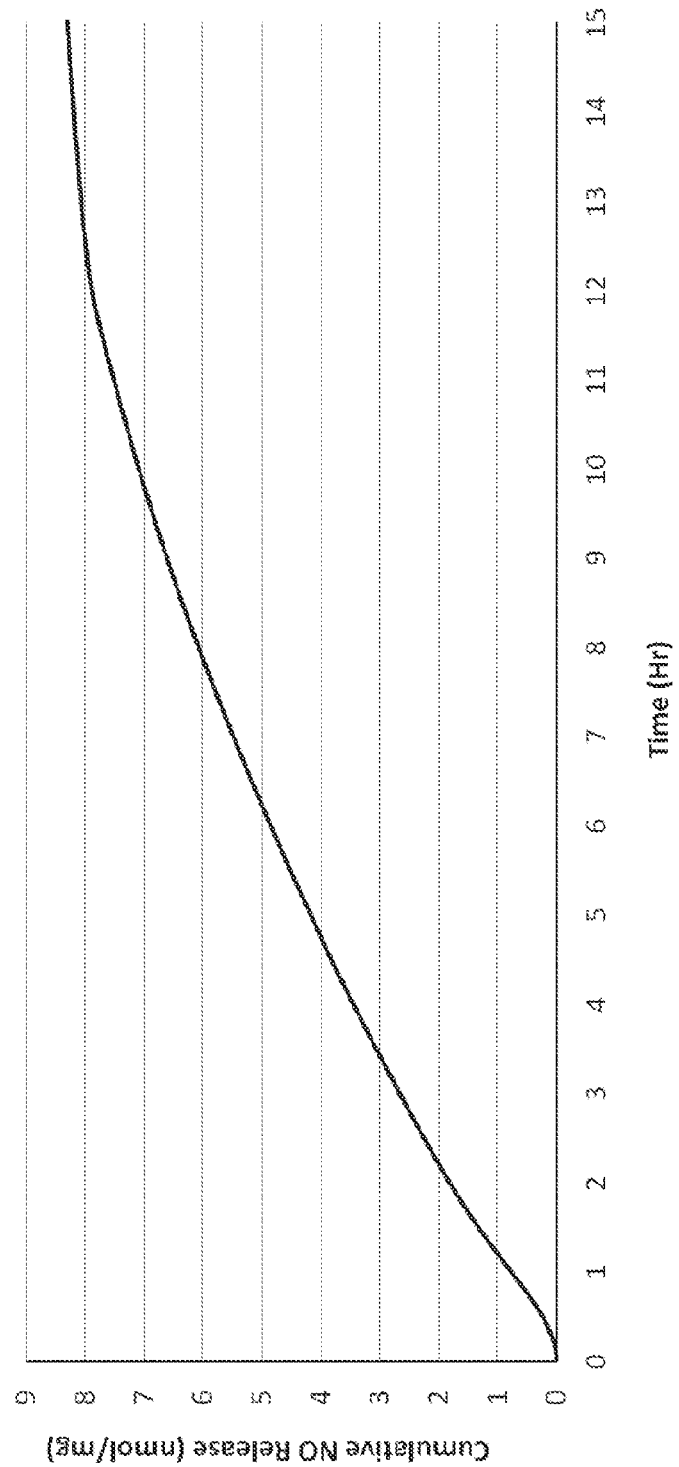
FIG. 7 shows the in vitro nitric oxide release profile for a 2% Nitricil™ NVN1 Gel formulation over time.
Figure 8:
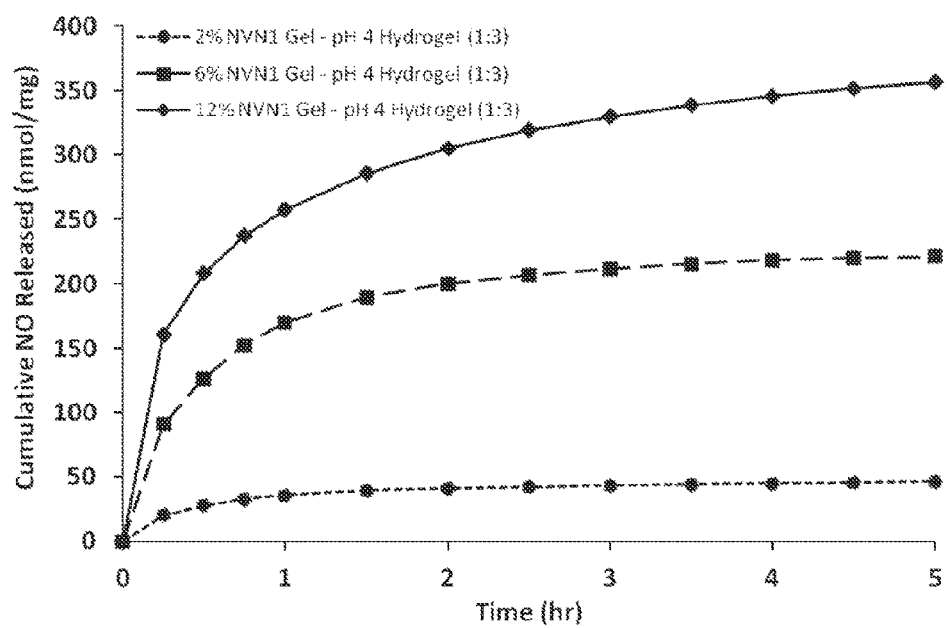
FIG. 8 shows the in vitro nitric oxide release profiles for 2%, 6%, and 12% Nitricil™ NVN1 Gel formulations upon mixing with the hydrogel at pH 4 over time.

For example, the effect a composition of the present invention may have on the amount of NO released can be seen in FIGS. 7 and 8. FIG. 7 shows the in vitro nitric oxide release profile for a 2% Nitricil™ NVN1 Gel having a formulation as set forth in Table 1 over time. FIG. 8 shows the in vitro nitric oxide release profiles for the 2% Nitricil™ NVN1 Gel and a 6% and 12% Nitricil™ NVN1 Gel having formulations as set forth in Table 1 upon mixing with a first composition of the present invention at pH 4 having a formulation as set forth in Table 2 in a 1:3 ratio (gel:first composition) over time. As can be seen from FIGS. 7 and 8 the cumulative NO release for the 2% Nitricil™ NVN1 Gel increased when in contact with a first composition of the present invention.

TABLE 1

Composition of the 2%, 6%, and 12% Nitricil ™ NVN1 gels.

| | % w/w | | | |
|---|---|---|---|---|
| Component | Gel Vehicle | 2% | 6% | 12% |
| Isopropyl alcohol | 85.5 | 83.5 | 80.5 | 74.5 |
| Hexylene glycol | 10.0 | 10.0 | 10.0 | 10.0 |
| Cyclomethicone | 2.5 | 2.5 | 2.5 | 2.5 |
| Hydroxypropyl cellulose | 2.0 | 2.0 | 1.0 | 1.0 |
| Nitricil ™ NVN1 | 0 | 2.0 | 6.0 | 12.0 |

TABLE 2

Composition of the first composition with a pH of 4.

| Component | % w/w |
|---|---|
| Purified water | 89.1 |
| Glycerin | 10.0 |
| Carbopol ® 974P | 0.5 |
| Sorbic acid | 0.2 |
| Trolamine | 0.2 |

A composition of the present invention may comprise a first composition of the present invention and a second composition as described herein. As those of skill in the art will recognize, the amount or concentration of individual components in a composition of the present invention may vary depending on the amount of the first composition and second composition present in the composition (e.g., the ratio of the first composition and second composition present in the composition). In some embodiments, the ratio of a first composition of the present invention to a second composition in a composition of the present invention may be about 5:1 or less, in further embodiments, about 4:1 or less, about 3:1 or less, about 2:1 or less, about 1:1 or less, about 0.5:1 or less, or about 0.2:1 or less. In particular embodiments, the ratio may be about 3:1. In further embodiments, the ratio may be about 1:1.

In some embodiments, a composition of the present invention may comprise, consist essentially of, or consist of a polyhydric alcohol in an amount of about 1% to about 10% by weight of the composition, a first viscosity increasing agent in an amount of about 0.01% to about 3% by weight of the composition, water in an amount of about 30% to about 50% by weight of the composition, a second viscosity increasing agent in an amount of about 0.01% to about 10% by weight of the composition, an organic solvent in an amount of about 30% to about 50% by weight of the composition, a humectant present in the second composition in an amount of about 2% to about 10% by weight of the composition, a water repelling agent in an amount of about 0.1% to about 10% by weight of the composition, an NO-releasing API in an amount of about 0.5% to about 10% by weight of the composition, optionally a buffering agent in an amount of about 0.001% to about 1% by weight of the composition, optionally a preservative in an amount of about 0.001% to about 1% by weight of the composition, and optionally a neutralizing agent. The neutralizing agent may be present in an amount sufficient to provide the first part of the composition with a pH of about 3 to about 8. The composition may have a pH of less than about 11, such as, but not limited to, less than about 9.5, less than about 7, or less than about 6. The first and second viscosity increasing agents may be the same and/or different. In certain embodiments, the first viscosity increasing agent may be a carboxypolymethylene and the second viscosity increasing agent may be a cellulose, such as, but not limited to, hydroxypropyl cellulose. In some embodiments, the composition may be cosmetically elegant.

In some embodiments, a composition of the present invention may comprise, consist essentially of, or consist of a polyhydric alcohol in an amount of about 2% to about 7% by weight of the composition, a first viscosity increasing agent in an amount of about 0.1% to about 1% by weight of the composition, water in an amount of about 40% to about 45% by weight of the composition, a second viscosity increasing agent in an amount of about 0.1% to about 1% by weight of the composition, an organic solvent in an amount of about 35% to about 45% by weight of the composition, a humectant present in the second composition in an amount of about 2% to about 7% by weight of the composition, a water repelling agent in an amount of about 0.1% to about 5% by weight of the composition, an NO-releasing API in an amount of about 0.5% to about 10% by weight of the composition, optionally a buffering agent in an amount of about 0.01% to about 0.2% by weight of the composition, optionally a preservative in an amount of about 0.01% to about 0.3% by weight of the composition, and optionally a neutralizing agent. The neutralizing may be present in an amount sufficient to provide the first part of the composition with a pH of about 4 or about 6. The composition may have a pH of less than about 11, such as, but not limited to, less than about 9.5, less than about 7, or less than about 6. The first and second viscosity increasing agents may be the same and/or different. In certain embodiments, the first viscosity increasing agent may be a carboxypolymethylene and the second viscosity increasing agent may be a cellulose, such as, but not limited to, hydroxypropyl cellulose. In some embodiments, the composition may be cosmetically elegant. In certain embodiments, the composition may comprise a composition as set forth in Table 13.

A composition of the present invention may comprise at least two different viscosity increasing agents. One viscosity increasing agent may be present in the first part of a composition of the present invention and the other viscosity increasing agent may be present in the second part of the composition. In some embodiments, a composition of the present invention comprises a carboxypolymethylene and a cellulose, such as, but not limited to, hydroxypropyl cellulose. Carboxypolymethylene may be present in a first composition of the present invention and the cellulose may be present in a second composition, which may be combined to form a composition of the present invention. A composition of the present invention comprising at least two different viscosity increasing agents may provide a cosmetically elegant composition comprising an API, such as, but not limited to, a particulate API and/or an insoluble API (e.g., an aqueous and/or moisture insoluble API, such as, for example, benzoyl peroxide).

A composition of the present invention may provide a structure suitable for suspending an API, such as, but not limited to, a particulate API and/or an insoluble API. In some embodiments, a composition of the present invention may encapsulate an API, such as, but not limited to, a particulate API and/or an insoluble API. For example, a composition of the present invention may encapsulate an API in at least one viscosity increasing agent and/or may provide a structure suitable for encapsulating an API. A composition of the present invention may prevent and/or reduce agglomeration of an API in the composition. While not wishing to be bound to any particular theory, a first composition of the present invention may provide means for suspending and/or encapsulating an API and/or for preventing and/or reducing agglomeration of an API in the composition. For example, a first composition of the present invention may provide a structure (e.g., a gel matrix) suitable for suspending and/or encapsulating an API in a composition of the present invention and/or for preventing and/or reducing agglomeration of an API in a composition of the present invention.

A composition of the present invention may comprise an API, a carboxypolymethylene, and a cellulose and may be a cosmetically elegant composition. The composition may not be gritty and/or may have a reduced grittiness compared to the API in the absence of a composition of the present invention. The composition may not be tacky (i.e., sticky) and/or may have a reduced tackiness (i.e., stickiness) compared to the API in the absence of a composition of the present invention. The composition may have a reduced and/or increased stiffness (i.e., hardness) and/or may have an increased homogeneity compared to the API in the absence of a composition of the present invention. In some embodiments, a composition of the present invention may comprise an API and may be a cosmetically elegant, homogeneous composition. While not wishing to be bound to any particular theory, a first composition of the present invention may provide means for providing a cosmetically elegant, homogeneous composition. For example, a first composition of the present invention may provide a structure (e.g., a gel matrix) suitable for providing a cosmetically elegant, homogeneous composition.

The first part and/or composition of a composition of the present invention and the second part and/or composition of the composition of the present invention may be contacted (e.g., mixed, stirred, blended, homogenized, and the like) during the process of compounding the composition. The composition of the present invention may then be stored with the first part and/or composition and the second part and/or composition combined (e.g., in the same vessel and/or container).

A composition of the present invention may comprise an API that is difficult to formulate, such as, but not limited to, an API that is difficult to formulate for a topical composition. For example, the API may be a particulate API, an insoluble API (e.g., an aqueous and/or moisture insoluble API), a thermally unstable API, and/or a photosensitive API.

According to embodiments of the present invention, the preparation of two separate parts for a composition of the present invention may provide an improved composition. A composition of the present invention comprising at least two parts may allow for an API (e.g., an API that is difficult to formulate) to be prepared in one part and later combined with the second part to prepare a cosmetically elegant composition and/or a composition comprising a more stable API compared to the same API prepared in a composition formed with one part and/or in the absence of a composition of the present invention. The API may be more stable in that the API could have a greater activity compared to its activity in the absence of a composition of the present invention and/or the API may be stored for a longer period of time compared to its storage in the absence of a composition of the present invention. In some embodiments, a composition of the present invention comprising an API (e.g., an API that is difficult to formulate) may provide a more cosmetically elegant composition compared to the API in a composition in the absence of a composition of the present invention. For example, a composition of the present invention comprising a particulate API and/or an insoluble API may provide a less gritty composition and thereby a more cosmetically elegant composition.

According to embodiments of the present invention, a kit may be provided. In some embodiments, a kit of the present invention may comprise a first composition of the present invention and a second composition as described herein. The first composition may be a hydrogel. The first composition may comprise at least one polyhydric alcohol present in an amount of about 1% to about 30% by weight of the first composition, at least one viscosity increasing agent present in an amount of about 0.1% to about 5% by weight of the first composition, and water present in an amount of about 70% to about 99% by weight of the first composition. The second composition may comprise an API, such as, but not limited to, an NO releasing API. The API (e.g., an NO releasing API) may be present in the second composition at a concentration in an amount of 0.01% to 50% by weight of the second composition or any range therein, such as, but not limited to, in an amount of 0.1% to 30% by weight of the second composition or in an amount of 2% to 20% by weight of the second composition. In some embodiments, the second composition may comprise at least one viscosity increasing agent present in the second composition in an amount of about 0.5% to about 30% by weight of the second composition, at least one organic solvent present in the second composition in an amount of about 50% to about 90 by weight of the second composition, and at least one humectant present in the second composition in an amount of about 2% to about 20% by weight of the second composition. In particular embodiments, the second composition may comprise an anhydrous alcohol gel containing a nitric oxide-releasing polysiloxane macromolecule as described in International Application Publication No. WO 2013/006608.

In some embodiments, a kit of the present invention comprises an aqueous composition, an organic composition, and an API that may be stable and/or soluble in the aqueous composition and/or the organic composition. A kit of the present invention may be configured to mix the two compositions upon dispensing and/or for application to a subject and/or may be configured to provide a combined composition with, increased performance and/or activity of the API compared to the performance and/or activity of the API in the absence of one of the compositions and/or the combined composition.

A kit of the present invention may separately store a first composition of the present invention and a second composition. In some embodiments, a kit of the present invention may contact the first composition and second composition, such as, but not limited to, by mixing the compositions, prior to application to a subject.

A first composition of the present invention (e.g., a hydrogel of the present invention) and a second composition may be mixed together and then applied to the skin of a subject. In other embodiments, a second composition may be applied to the skin of a subject and then a first composition may be applied over the second composition or vice versa. In some embodiments, the ratio of a first composition to a second composition, which may be applied to a subject, may be about 5:1 or less, in further embodiments, about 4:1 or less, about 3:1 or less, about 2:1 or less or about 1:1. In particular embodiments, the ratio may be about 3:1. In further embodiments, the ratio may be about 1:1.

Providing a first composition and a second composition that are combined upon and/or during application to the skin of a subject may allow for a longer shelf life of a kit of the present invention than if the compositions were stored mixed together in the kit. For example, the formulation and loading of API in the second composition may provide a stable product with a long shelf life. Thus, for example, pH and water content of the second composition may be adjusted to reduce or minimize release of a water-activated API so as to provide a composition that is stable at room temperature. The first composition may then be combined with the second composition to adjust the combined pH and provide water to activate the API. The second composition may be combined with the first composition in differing ratios to provide a desired release, pH and/or dose in the combined composition. Such an approach may allow for a single manufacturing process to be utilized for production of a more complex and costly second composition and then particular products defined by the composition and/or quantity of the first composition with which the second composition is mixed.

As will be appreciated by those of skill in the art in light of the present disclosure, a first composition of the present invention (e.g., a hydrogel of the present invention) may provide means for adjusting the pH of a pharmaceutical composition as well as means for activating an API of a pharmaceutical composition. In particular embodiments, a first composition of the present invention may provide means for reducing the pH of an anhydrous pharmaceutical composition comprising a diazeniumdiolate modified co-condensed polysiloxane macromolecule. In further embodiments, a first composition of the present invention may provide means for releasing nitric oxide from an anhydrous pharmaceutical composition comprising a diazeniumdiolate modified co-condensed polysiloxane macromolecule.

According to some embodiments, a method of the present invention may comprise administering a composition of the present invention (e.g., a first composition of the present invention and a second composition as described herein) and/or first composition of the present invention (e.g., a hydrogel of the present invention) to the skin of a subject. In certain embodiments, the composition and/or first composition may be topically administered. The composition may comprise at least one API, such as, but not limited to, a nitric oxide-releasing active pharmaceutical ingredient; a second viscosity increasing agent; at least one organic solvent; at least one humectant; at least one polyhydric alcohol; a first viscosity increasing agent; at least one preservative; and water. A method of the present invention may comprise forming an admixture prior to and/or during administration of a composition of the present invention. An admixture may be prepared by mixing or combining a composition comprising at least one API, such as, but not limited to, a nitric oxide-releasing active pharmaceutical ingredient; a second viscosity increasing agent; at least one organic solvent; and at least one humectant, and a composition comprising at least one polyhydric alcohol; a first viscosity increasing agent; at least one preservative; and water.

A method of the present invention may comprise topically applying a first composition of the present invention to the skin of a subject in combination and/or admixture with a second composition. The second composition may comprise a nitric oxide-releasing active pharmaceutical ingredient.

In some embodiments, a method of the present invention comprises delivering a therapeutically effective amount of a composition of the present invention to the skin of a subject. As used herein, the term "therapeutically effective amount" refers to an amount of a composition of the present invention that elicits a therapeutically useful response in a subject. Those skilled in the art will appreciate that the therapeutic effects need not be complete or curative, as long as some benefit is provided to the subject. In some embodiments, a therapeutically effective amount of a composition of the present invention may include delivering a therapeutically effective amount of a component of the composition, such as, but not limited to, an active pharmaceutical ingredient (e.g., a nitric oxide-releasing API). Therefore, a therapeutically effective amount of nitric oxide may be delivered and/or administered by a composition of the present invention.

The present invention finds use in both veterinary and medical applications. Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and canaries), and birds in ovo.

The methods of the present invention may also be carried out on animal subjects, particularly mammalian subjects such as mice, rats, dogs, cats, livestock and horses for veterinary purposes, and/or for drug screening and drug development purposes.

In particular embodiments of the present invention, the subject is "in need of" a method of the present invention, e.g., the subject has been diagnosed with, is at risk for, and/or is believed to have a disease or disorder that may be treated using a method of the present invention. In some embodiments, the subject has a skin disorder, such as, but not limited to, acne, androgenetic alopecia, atopic dermatitis, seborrheic dermatitis, *tinea* infections, *candida* infections, bacterial infections, verruca vulgaris, and/or psoriasis. In some embodiments of the present invention, the subject has an inflammatory skin condition or disorder and/or infection (e.g., impetigo, leishmaniasis, etc.). In some embodiments, a composition of the present invention may be used to treat acne vulgaris. According to some embodiments, a composition and/or method of the present invention may reduce *P. acnes* counts, inflammatory lesions, and/or noninflammatory lesions in a subject. In some embodiments, a composition and/or method of the present invention may be used to treat any disease, disorder, and/or condition suitable for topical administration with a composition comprising an NO-releasing API and an alcohol excipient, such as, but not limited to, alopecia (e.g., androgenetic alopecia) and/or a wart (e.g., a common, plantar, flat, filiform, genital, mosaic, and/or periungual wart).

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom is achieved and/or there is a delay in the progression of the disease, disorder, and/or condition. In particular embodiments, the severity of a skin disorder (e.g., acne) may be reduced in a subject compared to the severity of the skin disorder in the absence of a method of the present invention. In other embodiments, a method of the present invention may prevent and/or treat against infection.

A composition of the present invention may be applied topically to any portion of a subject's skin. However, in some embodiments, the subject's face is treated by a method described herein. Furthermore, in some embodiments, the subject's trunk is treated by a method described herein. In some embodiments, the subject's hand(s), finger(s), foot, feet, toe(s), and/or genital(s) are treated by a method described herein.

According to some embodiments of the present invention, a method of treating acne vulgaris may be provided, the method comprising topically applying a composition of the present invention to the skin of a subject. A therapeutically effective amount of the composition may be applied. In some embodiments, the composition may comprise a nitric oxide-releasing active pharmaceutical ingredient in an amount of about 0.5% to about 10% by weight of the composition, such as, but not limited to, about 1% to about 8% or about 2% to about 6%. In certain embodiments, the composition may comprise a nitric oxide-releasing active pharmaceutical ingredient in an amount of about 0.5%, 1%, 2%, 3%, 4%, 5%, 6%, 7%, 8%, 9%, or 10%. The composition may store and/or release nitric oxide in an amount of about 0.05% to about 3% by weight of composition, such as, but not limited to, about 0.15% to about 2%, about 0.15% to about 1%, about 0.3% to about 1.2%. In certain embodiments, the composition may store and/or release nitric oxide in an amount of about 0.15%, 0.3%, 0.6%, 0.9%, 1%, 1.2%, 1.5%, 1.75%, 2%, 2.25%, 2.5%, 2.75%, or 3%.

According to further embodiments of the present invention, a method of reducing inflammatory and/or noninflammatory lesions in a subject may be provided comprising topically applying a composition of the present invention to the skin of the subject. A therapeutically effective amount of the composition may be applied. In some embodiments, the composition may comprise a nitric oxide-releasing active pharmaceutical ingredient in an amount of about 0.5% to about 10% by weight of the composition, such as, but not limited to, about 1% to about 8% or about 2% to about 6%. In certain embodiments, the composition may comprise a nitric oxide-releasing active pharmaceutical ingredient in an amount of about 0.5%, 1%, 2%, 3%, 4%, 5%, 6%, 7%, 8%, 9%, or 10%. The composition may store and/or release nitric oxide in an amount of about 0.05% to about 3% by weight of composition, such as, but not limited to, about 0.15% to about 2%, about 0.15% to about 1%, about 0.3% to about 1.2%. In certain embodiments, the composition may store and/or release nitric oxide in an amount of about 0.15%, 0.3%, 0.6%, 0.9%, 1%, 1.2%, 1.5%, 1.75%, 2%, 2.25%, 2.5%, 2.75%, or 3%.

The method of reducing inflammatory and/or noninflammatory lesions may comprise topically applying a combined composition of the present invention. In some embodiments, the method may reduce inflammatory and/or noninflammatory lesions by about 10% or greater, such as, but not limited to, about 15%, 20%, 25%, 30%, 35%, 40%, 45%, 50%, 55%, 60%, 65%, 70%, 75%, 80%, 85%, 90%, 95%, or more, over a defined period of time compared to a subject who did not apply a composition of the present invention over the same time period. In certain embodiments, the method may reduce inflammatory and/or noninflammatory lesions in a subject compared to a subject who did not apply a composition comprising a nitric oxide-releasing active pharmaceutical ingredient over the same period of time.

In some embodiments, a method of reducing inflammatory and/or noninflammatory lesions in a subject may be provided comprising topically applying a first composition of the present invention to the skin of the subject. The first composition may not comprise an API, such as, but not limited to, an NO-releasing API. A therapeutically effective amount of the first composition may be applied. The method of reducing inflammatory and/or noninflammatory lesions comprising topically applying a first composition of the present invention may reduce inflammatory and/or noninflammatory lesions by about 10% or greater, such as, but not limited to, about 15%, 20%, 25%, 30%, 35%, 40%, 45%, 50%, 55%, 60%, 65%, 70%, 75%, 80%, 85%, 90%, 95%, or more, over a defined period of time compared to a subject who did not apply a first composition of the present invention over the same time period.

In some embodiments, a method of the present invention may comprise topically applying a composition of the present invention comprising a nitric oxide-releasing active pharmaceutical ingredient, wherein the method may reduce inflammatory and/or noninflammatory lesions by about 10% or greater, such as, but not limited to, about 15%, 20%, 25%, 30%, 35%, 40%, 45%, 50%, 55%, 60%, 65%, 70%, 75%, 80%, 85%, 90%, 95%, or more, over a defined period of time compared to a subject who applied substantially the same composition without the nitric oxide-releasing active pharmaceutical ingredient.

In certain embodiments, the subject may see a reduction in inflammatory and/or noninflammatory lesions within 1, 2, 3, 4, 5, 6, 7, 8, 9, 10, 11, 12, 13, or more week(s). In some embodiments, the method may reduce inflammatory and/or noninflammatory lesions in the skin of the subject with 12 weeks or less, in some embodiments, within 8 weeks or less, and in further embodiments, within 4 weeks or less.

In some embodiments, a method of the present invention may reduce *P. acnes* counts in a subject administered and/or topically applying a composition of the present invention. In certain embodiments, a method of the present invention may reduce *P. acnes* counts by about 10% or greater, such as, but not limited to, about 15%, 20%, 25%, 30%, 35%, 40%, 45%, 50%, 55%, 60%, 65%, 70%, 75%, 80%, 85%, 90%, 95%, or more over a defined period of time compared to a subject who did not apply a composition of the present invention over the same time period. In some embodiments, the method may reduce *P. acnes* counts in a subject compared to a subject who did not apply a composition comprising a nitric oxide-releasing active pharmaceutical ingredient over the same period of time.

In certain embodiments, a reduction in *P. acnes* counts may occur within 1, 2, 3, 4, 5, 6, 7, 8, 9, 10, 11, 12, 13, or more week(s). In some embodiments, a method of the present invention may reduce *P. acnes* counts in the skin of the subject with 12 weeks or less, in some embodiments, within 8 weeks or less, and in further embodiments, within 4 weeks or less.

The present invention is explained in greater detail in the following non-limiting Examples.

EXAMPLES

Example 1

Unbuffered hydrogel formulations with pH values ranging between 3 and 7 were developed. Several pH 6 hydrogel formulations were manufactured with varying levels of carbomer Carbopol® 974P to investigate the effects on viscosity and gel rheology. The effect of preservatives such as sorbic acid, benzoic and parabens were also investigated on the unbuffered hydrogel rheology and viscosity. The manufactured hydrogel formulations were used in measuring the admixture pH values (Example 2) with Nitricil™ NVN1 topical gel formulations comprising isopropyl alcohol (IPA) and varying strengths of Nitricil™ NVN1, and in establishing in vitro nitric oxide (NO) release kinetics (Example 3). A buffered pH 4 hydrogel with 0.1% w/w citric acid using Carpobol® 980P and a buffered pH 6 hydrogel using Carbopol® ETD 2020NF polymer with 0.2% w/w 0.1M phosphate buffer were also formulated.

For all formulations provided in Tables 3 and 4, United States Pharmacopeia (USP) grade water and anhydrous glycerol were mixed in either a 0.5-L or 2-L glass beaker using an IKA overhead mixer at ambient temperature. For the hydrogel formulations containing a preservative such as sorbic acid, benzoic acid, and methyl- and propyl-paraben, the preservative was added to the water and glycerol solution and heated using a hot plate to 70° C. for complete dissolution to occur. Once dissolution occurred, the solution was cooled down to ambient temperature. The next step in each experiment was to slowly transfer a Carbopol® polymer to the beaker with constant agitation using a combination of overhead stirring and homogenization using the IKA T-18 mixer at speeds of 3-4 for 20-30 seconds. A clear solution formed after 20 minutes indicating complete polymer dissolution. While under continuous agitation, the pH of the un-neutralized mixture was measured initially and trolamine was used as a neutralizing agent in a quantity sufficient (QS) to adjust the pH to the desired value and thicken the hydrogel. Finally, once the desired pH was obtained, a final quantity of water was added to reach the desired target batch size. For Batch Lot 112331, titanium dioxide was introduced into the hydrogel as a masking agent.

TABLE 3

Unbuffered hydrogel formulations without a preservative

| | Hydrogel Formulation [% w/w composition] | | | | | |
|---|---|---|---|---|---|---|
| Ingredient | Batch lot: 112333 | Batch lot: 112335 | Batch lot: 112337 | Batch lot: 112339 | Batch lot: 112345 | Batch lot: 112353 |
| Anhydrous Glycerol, ACS | 10.0 | 10.0 | 10.0 | 10.0 | 10.0 | 10.0 |
| Carbomer Homopolymer Type A, NF, Carbopol ® 974P | 1.0 | 0.5 | 0.2 | 0.3 | 0.4 | 0.5 |
| Purified Water, USP | 86.5 | 86.5 | 86.5 | 86.5 | 85.0 | 85.0 |
| Trolamine, NF | QS to pH 7 | QS to pH 6 | QS to pH 6 | QS to pH 6 | QS to pH 4 | QS to pH 4 |
| Purified Water, USP (adjustment) | QS | QS | QS | QS | QS | QS |

TABLE 4

Unbuffered hydrogel formulations with a preservative.

| | Hydrogel Formulation [% w/w composition] | | | | | | |
|---|---|---|---|---|---|---|---|
| Ingredient | Batch lot: 112331 | Batch lot: 112355 | Batch lot: 112357 | Batch lot: 112359 | Batch lot: 112361 | Batch lot: 112363 | Batch lot: 112365 |
| Anhydrous Glycerol, ACS | 10.0 | 10.0 | 10.0 | 10.0 | 10.0 | 10.0 | 10.0 |
| Benzoic Acid, NF | 0.1 | — | — | — | — | — | — |
| Sorbic Acid, NF | 0.1 | — | 0.2 | 0.1 | 0.2 | 0.1 | — |
| Methyl paraben | — | 0.2 | — | — | — | — | 0.2 |
| Propyl paraben | — | 0.05 | — | — | — | — | 0.1 |
| Carbomer Homopolymer Type A, NF, Carbopol 974P | 1.5 | 0.5 | 0.5 | 0.75 | 0.35 | 0.7 | 0.5 |
| Purified Water, USP | 85.0 | 85.0 | 86.5 | 86.5 | 86.5 | 86.5 | 85.0 |
| Titanium dioxide, NF | 0.05 | — | — | — | — | — | — |
| Trolamine, NF | QS to pH 3 | QS to pH 4 | QS to pH 4 | QS to pH 4 | QS to pH 4 | QS to pH 5 | QS to pH 5 |
| Purified Water, USP (adjustment) | QS | QS | QS | QS | QS | QS | QS |

The pH of un-neutralized mixtures with and without preservatives containing anionic Carbopol® polymer 974P was approximately 2.75-3 depending on the polymer concentration. The viscosity of the pH 3 hydrogel was found to be very low as only a small quantity of trolamine was added to adjust the pH to 3 units and therefore the thickening effects were not realized. To fully neutralize the Carbopol® 974P polymer a pH adjustment to 6 or 7 was necessary using trolamine. However, the viscosity of the resultant unbuffered hydrogels was very high at pH 6 and 7. While not wishing to be bound to any particular theory, for dispensing purposes, the concentration of Carbopol® 974P polymer may need to be reduced from 1% w/w to 0.3-0.5% w/w to lower the viscosity at pH 6 and 7. Using Carbopol® 974P polymer concentrations less than 0.3% w/w, while not wishing to be bound to any particular theory, may result in a hydrogel that is not viscous enough and may run off the surface of the skin when applied.

A pH 4 unbuffered hydrogel can be formulated with 0.5% w/w Carbopol® and have adequate viscosity and rheological properties to flow and dispense from a pump but also not run off the surface of the skin when applied. Table 5 shows the viscosity measurements of several unbuffered pH 4 and pH 5 hydrogels containing preservative(s) as described in Table 4.

TABLE 5

Viscosity measurements for unbuffered hydrogels with a preservative.

| Batch Lot | Viscosity [cP] |
|---|---|
| 112355 | 12675 |
| 112357 | 6961 |
| 112359 | 8631 |
| 112361 | 9372 |
| 112363 | 18376 |
| 112365 | 20746 |

The pH 4 hydrogels with a preservative had a viscosity ranging from 7000-12500 cP. The addition of preservative influenced the pH and therefore the neutralization (thickening) process using trolamine. Without wishing to be bound to any particular theory, to account for the presence of preservative and various concentrations of preservative, the level of Carbopol® polymer may need to be adjusted accordingly to obtain consistent viscosity post neutralization with base. Increasing the pH to 5 for an unbuffered hydrogel with preservative resulted in a significant increase in viscosity to approximately 20000 cP.

With Carbopol® 974P polymer, several buffering acids such as citric acid, tartaric acid and lactic acid were used to buffer at a pH of 4, but the hydrogels would instantaneously break down into water. Carbopol® ETD 2020, NF polymer was found to not be suitable for use with buffering agents at concentrations of 1-3% w/w.

A phosphate buffered pH 6 hydrogel was manufactured using 0.2% w/w Carbopol® ETD 2020 NF polymer in USP water and anhydrous glycerol. A 0.1 M stock of potassium phosphate buffer was added at 0.2% w/w to buffer the hydrogel at a pH of 6 units. This hydrogel was used with Nitricil™ NVN1 topical gels containing IPA and various strengths of Nitricil™ NVN1 to determine admixture pH in vitro (Example 2). The pH 6 phosphate buffered hydrogel had the effect of reducing the pH by 0.5 units at several different Nitricil™ NVN1 concentrations ranging from 0.2% to 8% w/w.

A citric acid buffered pH 4 hydrogel containing 0.1% w/w benzoic acid and 0.1% sorbic acid with 1% w/w Carbopol® polymer 980P was successfully compounded at a 0.5-kg scale. The composition of the buffered citric acid hydrogel is listed in Table 6. This buffered hydrogel (Batch lot: 126335) was measured to have a viscosity of 7285 cP. The citric acid buffered hydrogel manufactured was used to determine in vitro and skin surface pH (Example 2) including establishing in vitro nitric oxide release profiles (Example 3).

TABLE 6

Ingredient list and composition of the citric acid buffered pH 4 hydrogel.

| Hydrogel ingredient (Batch lot: 126335) | % w/w composition |
|---|---|
| Anhydrous Glycerol, ACS | 10.0 |
| Benzoic Acid, NF | 0.1 |
| Sorbic Acid, NF | 0.1 |
| Citric acid | 0.1 |
| Carbomer Homopolymer Type C, NF, Carbopol 980P | 1 |
| Purified Water, USP | 70 |
| Trolamine, NF | QS to pH4 |
| Purified Water, USP (adjustment A) | 10 |
| Purified Water, USP (adjustment B) | QS |

Hydrogel formulations covering a range of pH values were formulated. The initial hydrogels formulated were unbuffered and compounded with and without preservatives. Preservatives such as benzoic acid, sorbic acid and parabens were used. Parabens were found to react with Nitricil™ NVN1 IPA topical gels. The pH of the hydrogels was adjusted by varying the quantity of trolamine (neutralizing agent) added. To increase the pH and viscosity, the amount of neutralizing agent added was increased. At pH 6 and 7, the viscosity of the unbuffered hydrogels without preservatives formed was high. In order to reduce the hydrogel viscosity, the Carbopol® polymer concentration was reduced. The addition of preservatives also influenced the initial pH. The amount of polymer and neutralizing agent was adjusted accordingly to reach the desired pH and obtain a viscosity that is not too low as to cause issues with runoff from the surface of the skin and not too high such as to cause issues with product flow and pumping from a dual chamber dispensing device. Attempts were made to manufacture a buffered pH 4 hydrogel using Carpobol® 974P and ETD 2020 polymer with citric acid, lactic acid, and tartaric acid as buffering agents but this resulted in the polymers breaking down into water due to rapid changes in pH.

By switching to Carbopol® 980P, which is a Homopolymer Type C and a longer chain polymer, a 0.1% w/w citric acid buffered pH 4 hydrogel with sorbic acid and benzoic acid was successfully formulated. A pH 6 hydrogel that was buffered with 0.1 M phosphate buffer at 0.2% w/w was also successfully formulated with Carbopol® ETD 2020 polymer.

Example 2

A series of experiments were carried out to determine the final admixture pH of Nitricil™ NVN1 topical gels containing IPA and having different strengths of Nitricil™ NVN1 ranging from 0.2-12% w/w with unbuffered and buffered hydrogel formulations having a pH ranging from 4 to 6 at different hydrogel to Nitricil™ NVN1 topical gel ratios ranging from 1:1 to 3:1 (Hydrogel to Nitricil™ NVN1 topical gel). The effect of hydrogel pH, mixing ratio of hydrogel to Nitricil™ NVN1 IPA topical gel, and Nitricil™ NVN1 strength on the final admixture pH was investigated. The aim of the experiments was to determine whether a final admixture pH ranging between 6 to 8 could be obtained.

For all in vitro pH admixture measurements, approximately 1-g quantity of Nitricil™ NVN1 Topical IPA Gel was dispensed into a tared weigh boat using either a 1 mL plastic syringe or directly dispensed from aluminum tubes. Once approximately 1 g quantity was dispensed, the weigh boat was re-tared. A pre-determined quantity of hydrogel ranging from 1 to 3-g was then dispensed into the weigh boat using a 1 mL syringe. The admixture was then mixed using pH probe (Beckman ϕ350 pH meter) until a single steady state pH measurement was recorded. All dispensing was done on a weight basis.

A pH 6 phosphate buffered hydrogel, an unbuffered pH 4 hydrogel, and an unbuffered pH 6 hydrogel were used to determine admixture pH values as shown in Table 7.

TABLE 7

Hydrogel formulations used in the initial admixture pH determinations.

| | % w/w | | |
|---|---|---|---|
| Ingredient | pH 4 | pH 6 | pH 6 (Buffered) |
| Purified Water, USP | 85.0 | 85.0 | 85.0 |
| Glycerol, NF | 10.0 | 10.0 | 10.0 |
| Carbomer Homopolymer Type A, NF Carbopol 974P | 1.0 | 0.3 | — |
| Carbomer Interpolymer Type B, NF Carbopol ETD2020NF | — | — | 0.5 |
| Trolamine, NF | QS to pH 4 | QS to pH 6 | QS to pH 6 |
| Purified Water, USP | QS | QS | — |
| 0.1M Phosphate Buffer (pH 6.0) | — | — | QS |

FIG. 1 shows the effect of Nitricil™ NVN1 Topical Gel strength, hydrogel pH, and hydrogel to Nitricil™ NVN1 IPA Topical Gel ratio on the admixture pH. The admixture pH results demonstrate that in order to achieve a pH of 8 for the final admixture, Nitricil™ NVN1 Topical Gel at or below 6% w/w Nitricil™ NVN1 could be used in combination with the hydrogel pH 4 at either a 1:1 or 3:1 ratio. At strengths of 8% w/w Nitricil™ NVN1 or greater, the strong buffering properties of Nitricil™ NVN1 start to heavily influence the pH of the admixture over the range of hydrogel pH's and ratios evaluated. Significant foaming (indicating nitric oxide release) was observed at strengths greater than 4% w/w Nitricil™ NVN1 when mixing with both pH 4 and pH 6 hydrogels. This was observed even at high pH admixture values greater than 8 when using pH 6 hydrogels. The 1:3 ratio of Nitricil™ NVN1 Topical Gel and hydrogel buffered at pH 6 allowed the resulting pH of the admixture to be maintained below pH 8 for Nitricil™ NVN1 Topical Gel strengths up to 2% w/w Nitricil™ NVN1. Buffering the hydrogel with phosphate at pH 6 helped reduce the final admixture pH at both 1:1 and 1:3 mixing ratios of hydrogel to Nitricil™ NVN1 IPA Topical Gel.

Further experiments investigated the effect of adding preservatives (e.g., parabens, sorbic acid and benzoic acid) at concentrations ranging between 0.1% to 0.2% w/w to hydrogel formulations adjusted to pH 4 and pH 5. The admixture pH was measured for Nitricil™ NVN1 Topical Gel strengths at 2% w/w and 8% w/w.

Table 8 shows the admixture pH values using both 2% and 8% w/w Nitricil™ NVN1. The results in Table 8 show that the 2% w/w Nitricil™ NVN1 IPA Topical Gel with the pH 4 hydrogel, with and without preservatives, at a ratio of 1:1 provided a resultant admixture pH between 6 and 7.

TABLE 8

Admixture pH values for different pH hydrogels with and without preservative.

| Nitricil™ NVN1 [% w/w] | Hydrogel pH | Preservative | Concentration [% w/w] | Admixture pH |
|---|---|---|---|---|
| 2 | 4 | Methyl- and Propyl-paraben | 0.25 | 6.61 (Gel mixture turns brown) |
| 2 | 4 | Sorbic acid | 0.2 | 5.89 |
| 2 | 4 | Sorbic acid | 0.1 | 6.73 |
| 2 | 4 | No preservative | — | 6.78 |
| 8 | 4 | 0.2% methyl- and 0.5% propyl-paraben | 0.25 | 9.93 |
| 8 | 4 | Sorbic acid | 0.2 | 10.19 |
| 8 | 4 | Sorbic acid | 0.1 | 10.27 |
| 8 | 4 | None | — | 8.25 |
| 8 | 4 | None | — | 10.80 |
| 2 | 5 | Methyl- and Propyl-paraben | 0.25 | 7.15 (Gel mixture turns brown) |
| 2 | 5 | Sorbic acid | 0.2 | 6.81 |
| 2 | 5 | Sorbic acid | 0.1 | 6.94 |

Using methyl- and propyl-paraben as preservatives resulted in the admixture turning brown. Without wishing to be bound to any particular theory, this could be indicative of the formation of degradation product(s). Using pH 5 hydrogels with different preservatives, the admixture pH only increased marginally to about 7.

The surface skin pH of the admixture was also measured for 8% w/w Nitricil™ NVN1 Topical IPA Gel with both a buffered and unbuffered pH 4 hydrogel. The buffered pH 4 hydrogel contained Carbopol® 980P NF polymer with 0.1% w/w citric acid. Benzoic acid and sorbic acid at 0.1% w/w were also used as preservatives in the citric acid buffered pH4 formulated hydrogel.

Figure 2:
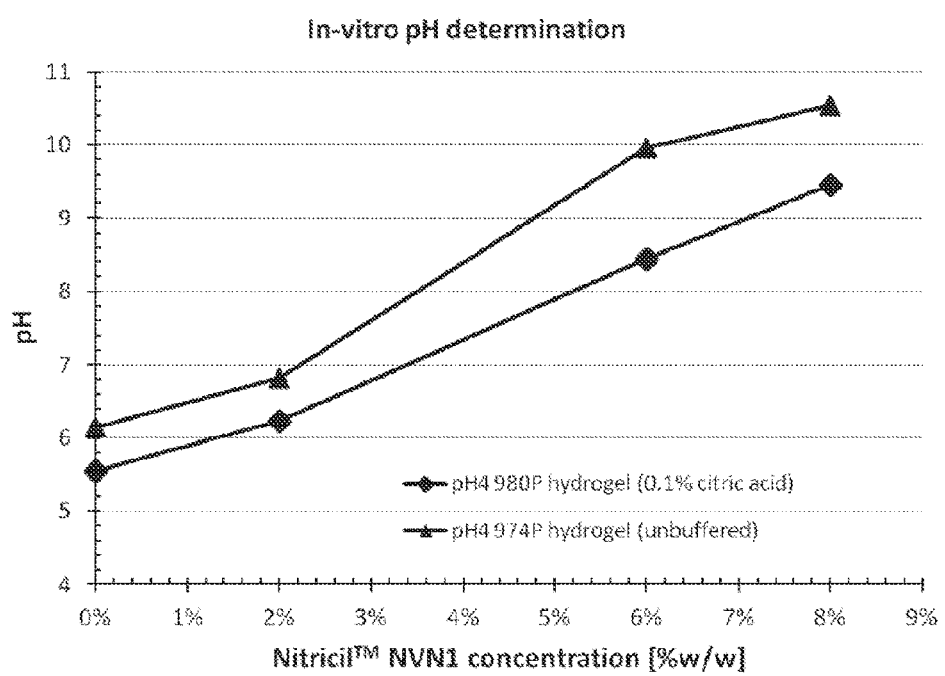
FIG. 2 shows a graph of the in vitro pH determination for Nitricil™ NVN1 topical gels when admixed with an unbuffered or buffered (0.1% citric acid) hydrogel (pH 4).

Further in vitro pH admixture measurements were taken with an unbuffered pH 4 hydrogel (Carbopol® 974P) and buffered pH 4 hydrogel with 0.1% w/w citric acid (Carbopol® 980P) at a 1:1 ratio to confirm observations made from experimental results in Table 8. FIG. 2 shows that at 6% w/w and 8% w/w Nitricil™ NVN1 concentrations when used with an unbuffered pH 4 hydrogel, the admixture pH is around 10 and is comparable with previous results. The use of 0.1% w/w citric acid buffered pH 4 hydrogel has the effect of reducing the admixture pH over a range of Nitricil™ NVN1 concentrations.

Figure 3:
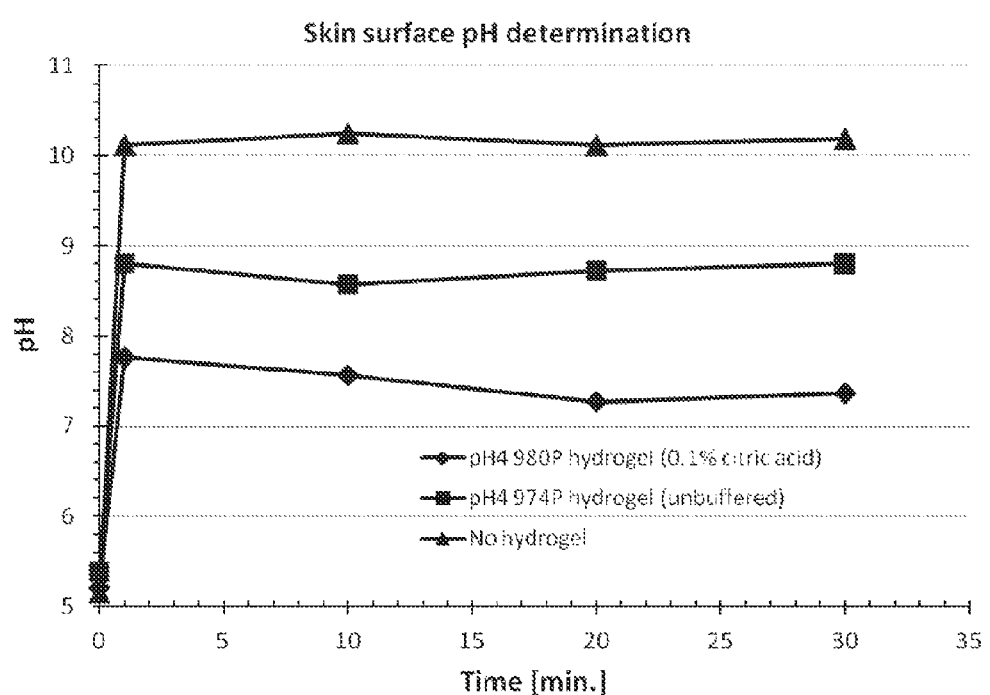
FIG. 3 shows a graph of the skin surface pH determination for admixtures of an unbuffered or buffered pH 4 hydrogel and an 8% w/w Nitricil™ NVN1 Topical Gel.

An in vitro skin surface pH determination investigation was also performed. FIG. 3 shows that the skin, which has a pH range of between 5 and 6, provides some degree of buffering capability. Application of an unbuffered pH 4 hydrogel mixed with the 8% w/w Nitricil™ NVN1 IPA Topical Gel resulted in a skin pH just below 9. The pH remained consistent over 30 minutes. However, when the pH 4 hydrogel buffered with 0.1% w/w citric acid was used (including 0.1% w/w benzoic acid and 0.1% w/w sorbic acid as preservatives) with the 8% w/w Nitricil™ NVN1 IPA Topical Gel, the skin surface pH was around 7.5.

Without wishing to be bound to any particular theory, the experiments demonstrate that with pH 4 buffered and unbuffered hydrogels at a 1:1 and 3:1 ratio, the final admixture pH can be maintained between 5 to 8 for Nitricil™ NVN1 concentrations ranging between 0.2% w/w and 4% w/w. With a pH 4 unbuffered hydrogel at a 3:1 ratio it is possible to maintain the admixture pH below 8 units for Nitricil™ NVN1 concentrations up to 8% w/w. With a buffered pH 6 hydrogel it is possible to maintain the pH below 8 at Nitricil™ NVN1 concentrations of 2% w/w or less. To maintain the admixture pH value below 8, a concentration of 1% w/w Nitricil™ NVN1 or less may be used with an unbuffered pH 6 hydrogel. The use of preservatives in hydrogels has no to little effect on the admixture pH. The use of pH 4 hydrogels that are unbuffered and buffered at a ratio of 1:1 resulted in pH values greater than 8 units. However, when applied to the skin the pH measurement at the surface decreases as the skin offers some buffering capacity. To obtain a skin surface admixture pH less than 8 units, a pH 4 hydrogel that is buffered with 0.1% w/w citric acid and containing 0.1% w/w benzoic acid and sorbic acid can be used. However, an unbuffered pH 4 hydrogel gave a skin surface pH value of greater than 8.5 when compared to pH of 10 units from in vitro testing results.

Example 3

In vitro release testing was performed using both a single channel and multichannel Nitric Oxide Analyzer. An analytical balance was used to weight Nitricil™ NVN1 Topical Gel and hydrogel samples. Approximately 50-mg of the Nitricil™ NVN1 Topical Gel sample and either ~50 mg or ~150 mg hydrogel sample were transferred to a single, pre-cut weigh boat without allowing contact between the samples. The two samples were mixed for approximately 5 sec., and then immediately placed into a clean, dry 50-mL NO measurement cell maintained at 37° C. The real-time in vitro release of nitric oxide from the combined Nitricil™

NVN1 Topical Gel/Hydrogel samples was determined using the following instrumental parameters:
1. Moist Nitrogen Flow Rate: 112-115 ml/min
2. Sample Temperature: 37° C.
3. Detection: Nitric Oxide by Chemiluminescence
4. Data Acquisition Frequency: 1 Hz, Irregular Sequential Alternating
5. Duration: Time at which NO release rate decreases linearly (NLT 8 hr)
6. Acquisition Software: NovanWare v 1.05

Conversion from parts per billion (PPB) NO to moles nitric oxide was achieved by measuring the nitric oxide generated from a known amount of sodium nitrite in a solution of potassium iodide to acquire a PPB-to-mole conversion factor. Any gaps in real-time nitric oxide release data resulting from multichannel operation were filled in by using a linear interpolation program. For any sample that was not measured to exhaustion of nitric oxide, a linear extrapolation to zero release of the last ~5000 sec of release was performed. Real-time nitric oxide release data was then integrated, resulting in a total nitric oxide accumulation curve. Nitric oxide release parameters such as $C_{max}$ (i.e., the maximum concentration of NO released), $T_{max}$ (i.e., the time at which $C_{max}$ is achieved), Cumulative Nitric Oxide Released (i.e., the sum of all data points per unit time), and Time to Half of Total Released ($T_{50}$) (i.e., the time at which 50% of the cumulative NO is released) were calculated from both the real time and total accumulation nitric oxide release curves. All of the above calculations were performed automatically in custom-built data processing software (NovanWare v 1.05).

The results from in vitro release testing, along with the respective pH of the admixtures are summarized in Table 9 below.

Figure 4:
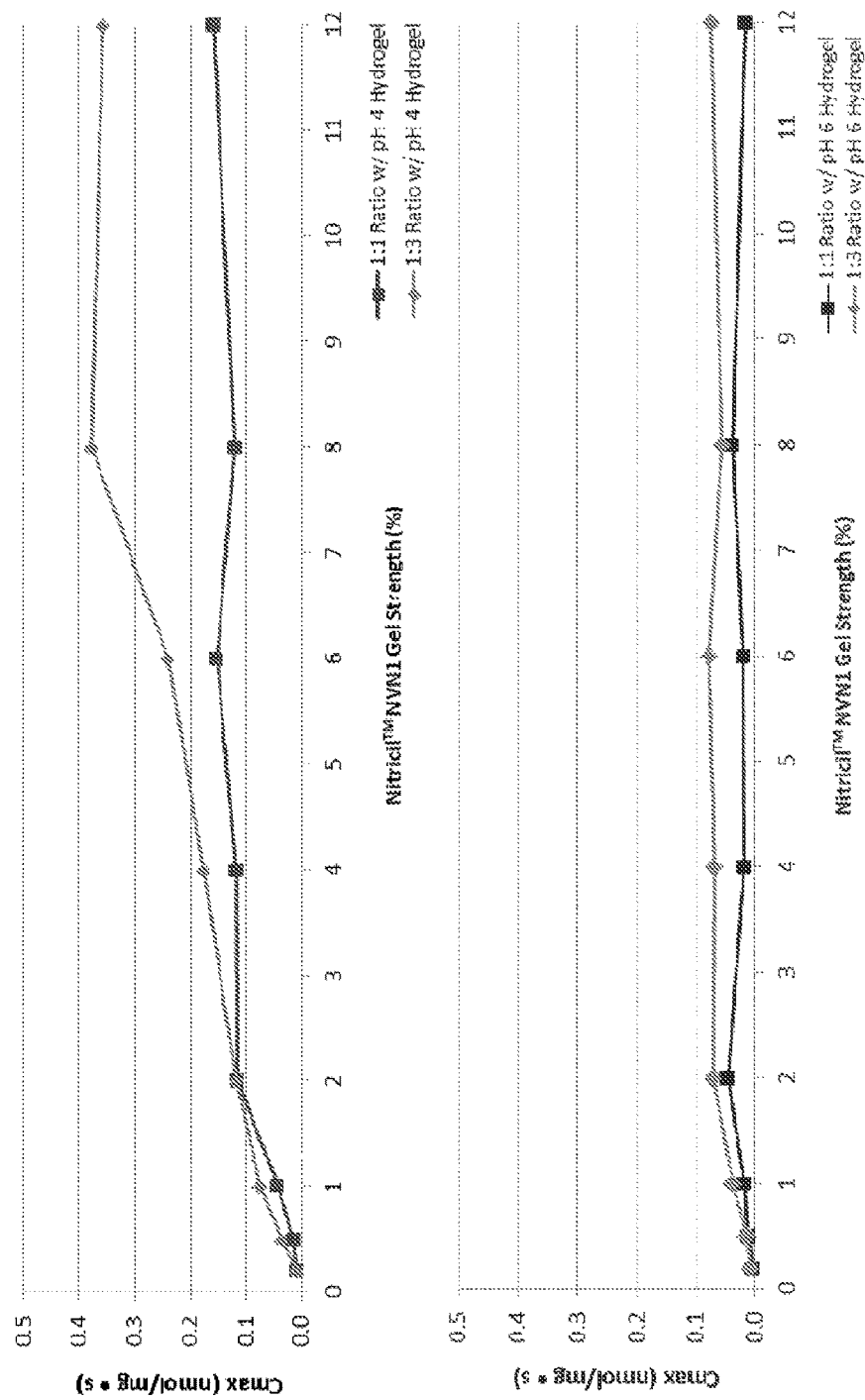
FIG. 4 shows a graph of the effects of Nitricil™ NVN1 Topical Gel strength and hydrogel ratio on $C_{max}$.
Figure 5:
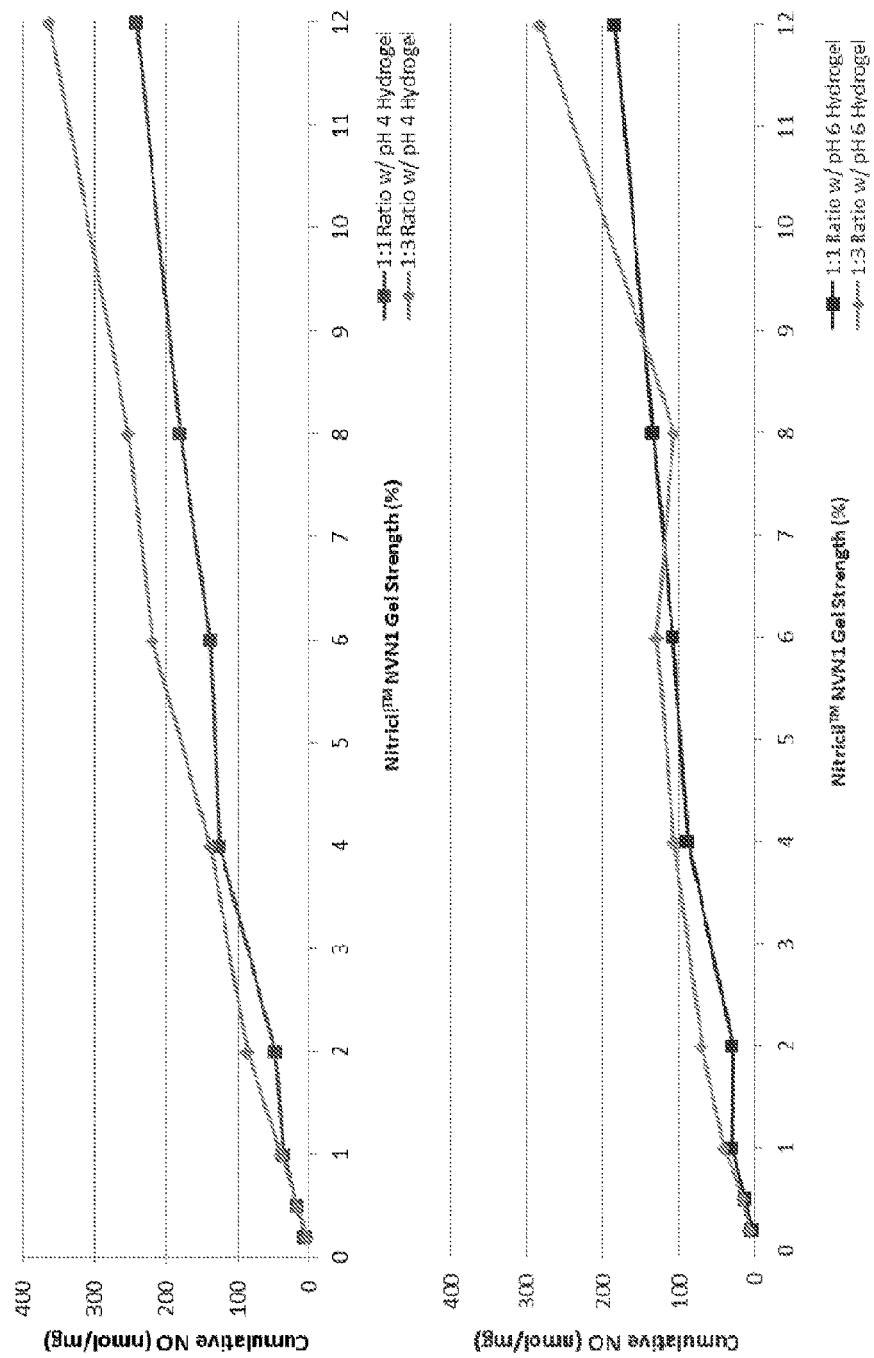
FIG. 5 shows a graph of the effects of Nitricil™ NVN1 Topical Gel strength and hydrogel ratio on cumulative nitric oxide (NO) release.

FIG. 4 illustrates how $C_{max}$ from each mixture is impacted by the ratio of the mixture, the pH of the hydrogel, and the concentration of NVN1. In general, for pH 4 hydrogels the $C_{max}$ increased with increasing NVN1 concentration. This effect is more pronounced with mixtures containing 1:3 Nitricil™ NVN1 IPA Topical Gel to hydrogel. FIG. 5 shows the increase in cumulative nitric oxide released with increasing Nitricil™ NVN1 concentrations.

Figure 6:
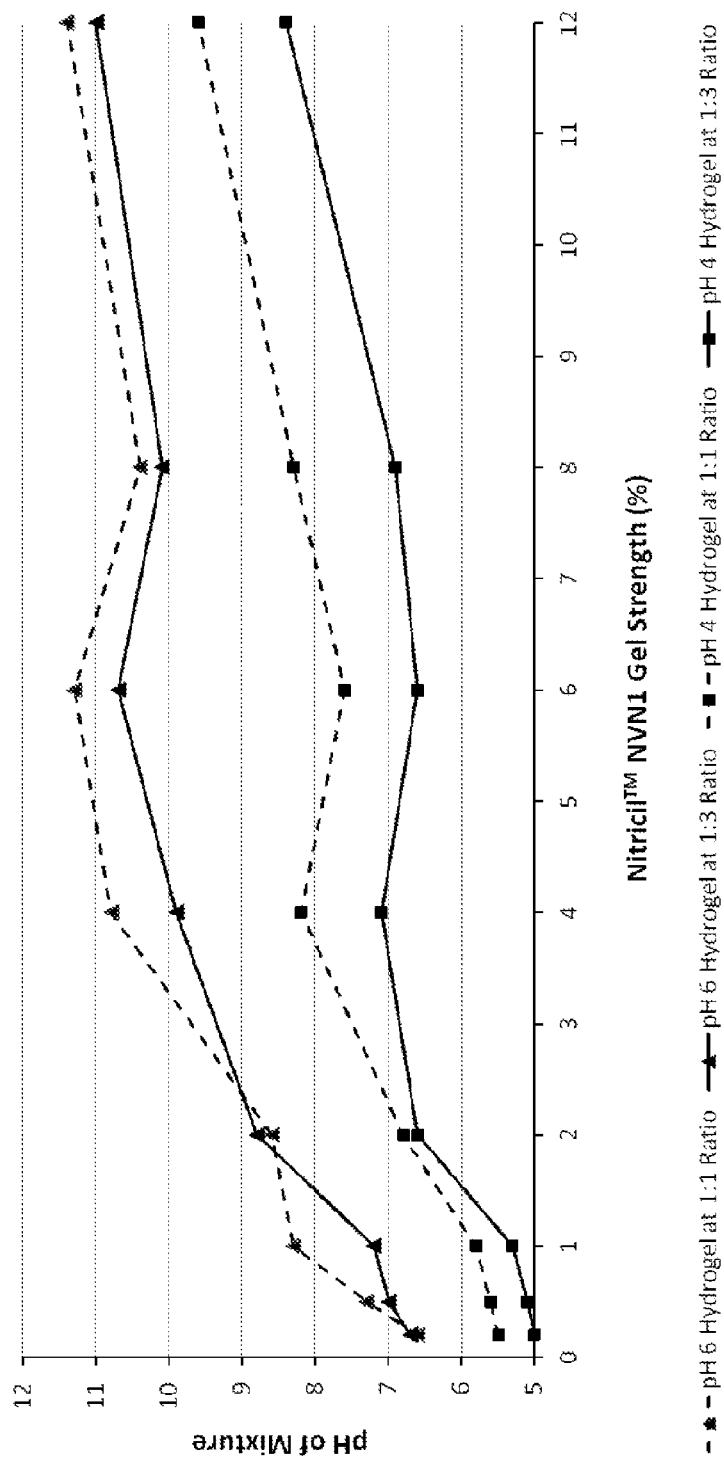
FIG. 6 shows a graph of the effects of unbuffered hydrogel pH and ratio on admixture pH with respect to Nitricil™ NVN1 Topical Gel strength.

At all Nitricil™ NVN1 concentrations, mixtures containing pH 4 hydrogels generally release more of their nitric oxide payload at higher $C_{max}$ (FIG. 4) and with a shorter half-life than with pH 6 hydrogels. This effect is more pronounced for mixtures containing a 1:3 ratio with a pH 4 hydrogel versus 1:1 and 1:3 ratios with a pH 6 hydrogel. FIG. 6 shows the effects of unbuffered hydrogel pH and ratio on admixture pH with respect to Nitricil™ NVN1 Topical Gel strength. Further in vitro studies were performed using a pH 4 buffered citric acid hydrogel with preservative. Measurements were repeated in triplicate. The admixture was mixed for a period of 15 seconds prior to loading into the measurement cell. The results for the in vitro nitric oxide release tests are shown in Table 10.

TABLE 9

Results summary for pH and in vitro release testing of Nitricil ™ NVN1 topical gel.

| Sample | Ratio | $C_{max}$ (nmol/mg/s) | Cumulative NO (nmol/mg) | $T_{max}$ (min) | $T_{50}$ (min) | pH |
|---|---|---|---|---|---|---|
| 0.2% Gel/Hydrogel pH 4 | 1:1 | 0.009 | 5 | 1 | 14 | 5.5 |
| 0.2% Gel/Hydrogel pH 4 | 1:3 | 0.008 | 4 | 1 | 13 | 5.0 |
| 0.2% Gel/Hydrogel pH 6 | 1:1 | 0.003 | 4 | 1 | 52 | 6.6 |
| 0.2% Gel/Hydrogel pH 6 | 1:3 | 0.007 | 6 | 1 | 37 | 6.7 |
| 0.5% Gel/Hydrogel pH 4 | 1:1 | 0.016 | 17 | 2 | 23 | 5.6 |
| 0.5% Gel/Hydrogel pH 4 | 1:3 | 0.037 | 17 | 1 | 7 | 5.1 |
| 0.5% Gel/Hydrogel pH 6 | 1:1 | 0.011 | 12 | 2 | 30 | 7.3 |
| 0.5% Gel/Hydrogel pH 6 | 1:3 | 0.014 | 15 | 1 | 41 | 7.0 |
| 1% Gel/Hydrogel pH 4 | 1:1 | 0.042 | 37 | 2 | 17 | 5.8 |
| 1% Gel/Hydrogel pH 4 | 1:3 | 0.075 | 39 | 1 | 8 | 5.3 |
| 1% Gel/Hydrogel pH 6 | 1:1 | 0.018 | 30 | 3 | 43 | 8.3 |
| 1% Gel/Hydrogel pH 6 | 1:3 | 0.038 | 41 | 2 | 51 | 7.2 |
| 2% Gel/Hydrogel pH 4 | 1:1 | 0.092 | 73 | 1 | 24 | 6.8 |
| 2% Gel/Hydrogel pH 4 | 1:3 | 0.062 | 50 | 1 | 24 | 5.5 |
| 2% Gel/Hydrogel pH 6 | 1:1 | 0.045 | 29 | 1 | 50 | 8.6 |
| 2% Gel/Hydrogel pH 6 | 1:3 | 0.070 | 71 | 2 | 58 | 8.8 |
| 4% Gel/Hydrogel pH 4 | 1:1 | 0.118 | 126 | 1 | 36 | 8.2 |
| 4% Gel/Hydrogel pH 4 | 1:3 | 0.175 | 138 | 2 | 18 | 7.1 |
| 4% Gel/Hydrogel pH 6 | 1:1 | 0.018 | 88 | 3 | 230 | 10.8 |
| 4% Gel/Hydrogel pH 6 | 1:3 | 0.068 | 107 | 2 | 71 | 9.9 |
| 6% Gel/Hydrogel pH 4 | 1:1 | 0.151 | 138 | 2 | 23 | 7.6 |
| 6% Gel/Hydrogel pH 4 | 1:3 | 0.240 | 220 | 1 | 25 | 6.6 |
| 6%/Hydrogel pH 6 | 1:1 | 0.020 | 109 | 3 | 155 | 11.3 |
| 6%/Hydrogel pH 6 | 1:3 | 0.077 | 129 | 2 | 43 | 10.5 |
| 8% Gel/Hydrogel pH 4 | 1:1 | 0.120 | 180 | 1 | 67 | 8.3 |
| 8% Gel/Hydrogel pH 4 | 1:3 | 0.187 | 239 | 1 | 25 | 6.9 |
| 8%/Hydrogel pH 6 | 1:1 | 0.037 | 134 | 5 | 247 | 10.4 |
| 8%/Hydrogel pH 6 | 1:3 | 0.056 | 109 | 9 | 43 | 10.1 |
| 12% Gel/Hydrogel pH 4 | 1:1 | 0.159 | 242 | 3 | 94 | 9.6 |
| 12% Gel/Hydrogel pH 4 | 1:3 | 0.357 | 364 | 5 | 28 | 8.4 |
| 12% Gel/Hydrogel pH 6 | 1:1 | 0.016 | 184 | 5 | 371 | 11.4 |
| 12% Gel/Hydrogel pH 6 | 1:3 | 0.074 | 282 | 5 | 166 | 11.0 |

TABLE 10

Results summary for pH and in vitro release testing of Nitricil ™ NVN1 topical gel using citric acid pH 4 buffered hydrogel.

| Sample | $C_{max}$ (nmol/mg · s) | Cumulative NO (nmol/mg) | $T_{max}$ (min) | $T_{50}$ (min) | pH of Mixture |
|---|---|---|---|---|---|
| 2% Gel/Hydrogel pH 4 (citric acid buffer) #1 | 0.162 | 71 | 1 | 8 | 6.2 |
| 2% Gel/Hydrogel pH 4 (citric acid buffer) #2 | 0.109 | 59 | 1 | 10 | |
| 2% Gel/Hydrogel pH 4 (citric acid buffer) #3 | 0.148 | 60 | 1 | 8 | |
| Average | 0.140 | 63 | 1 | 9 | |
| 8% Gel/Hydrogel pH 4 (citric acid buffer) #1 | 0.200 | 167 | 1 | 30 | 9.5 |
| 8% Gel/Hydrogel pH 4 (citric acid buffer) #2 | 0.218 | 182 | 1 | 26 | |
| 8% Gel/Hydrogel pH 4 (citric acid buffer) #3 | 0.250 | 185 | 1 | 23 | |
| Average | 0.256 | 178 | 1 | 26 | |

Example 4

A phase 1, multiple dose, single-center, observer-blind, randomized, parallel group, safety and cutaneous tolerability study was conducted in 60 healthy volunteers. The objectives of this study were to evaluate the safety and cutaneous tolerability of multiple concentrations of Nitricil™ NVN1.

The diagnosis and main criteria for inclusion into the study were healthy male and female volunteers 18 years of age and older with elevated *P. acnes* counts on the face as demonstrated by a high degree of fluorescence of the facial skin under a Wood's lamp.

Subjects, who had satisfied the entry criteria at the Screening/Baseline visit, were randomized to 2% Nitricil™ NVN1 Topical Gel, 4% Nitricil™ NVN1 Topical Gel, 8% Nitricil™ NVN1 Topical Gel or Topical Gel Vehicle in a 1:1:1:1 ratio (Table 11). Subjects returned once daily on the weekdays to apply the assigned treatment under supervision. Approximately 0.5 g was applied evenly over the entire face (3-4% total body surface area (TBSA)) after washing, sparing the eyes and mouth. On Saturday and Sunday, subjects applied the treatment (unsupervised) at home once daily. The dose of approximately 0.5 g was topically applied once daily for four weeks.

TABLE 11

Test article (2% Nitricil ™ NVN1 Topical Gel, 4% Nitricil ™ NVN1 Topical Gel, and 8% Nitricil ™ NVN1 Topical Gel) and reference (Topical Gel Vehicle) formulations.

| Ingredient | 2% Nitricil ™ NVN1 Topical Gel (% w/w) | 4% Nitricil ™ NVN1 Topical Gel (% w/w)[1] | 8% Nitricil ™ NVN1 Topical Gel (% w/w) | Topical Gel Vehicle (% w/w) |
|---|---|---|---|---|
| Isopropyl alcohol | 83.50 | 82.0x | 78.50 | 85.5 |
| Hexylene glycol | 10.00 | 10.0x | 10.00 | 10.00 |
| Cyclomethicone | 2.50 | 2.50 | 2.50 | 2.50 |
| Hydroxylpropyl cellulose | 2.00 | 1.50 | 1.00 | 2.00 |
| Nitricil ™ NVN1 | 2.00 | 4.00 | 8.00 | 0 |

[1]"x" denotes a non-significant FIGURE.

Assessments included cutaneous tolerability, blood chemistry and hematology, methemoglobin analysis, physical exams, urine pregnancy tests (UPTs), adverse event collection and collection of vital signs including blood pressure. *Propionobacterium acnes* (*P. acnes*) cultures from the central forehead were collected at Baseline, Week 2 and Week 4. Volunteers returned for post-baseline evaluation at Weeks 2 and 4/Early Termination (ET).

Tolerability and safety assessments included cutaneous tolerability evaluation, adverse events (AEs), methemoglobin measurements, physical examination including vital signs, and laboratory examination [blood chemistry, hematology and urine pregnancy tests (UPTs)].

*P. acnes* cultures were collected from the central forehead via a swab technique at Baseline (BL) Week 2, and Week 4 (Williamson 1965).

This was a preliminary study and was not powered for statistical significance. All statistical processing was to be performed using SAS® unless otherwise stated. Statistical significance was based on two-tailed tests of the null hypothesis resulting in p-values of 0.05 or less. Safety analyses were performed using the safety population.

Each Cutaneous Tolerability Scale was summarized categorically and continuously, by treatment group and visit. Within the categorical summary, a Cochran-Mantel-Haenszel test, using modified ridits, was performed for each post-baseline assessment.

Blood chemistry and hematology values were reported individually at Baseline and at Weeks 2 and 4/ET. Additionally, the change from baseline was reported at Week 2 and Week 4/ET. Labs were reported in SI units.

Methemoglobin was summarized categorically and continuously, by treatment group and visit. Additionally, boxplots were presented by treatment group and visit. The boxplots displayed the mean, median, minimum, maximum, first and third quartiles, with all observed data points overlayed upon the boxplot so that any outliers were easily visualized.

All AEs occurring during the study were recorded and classified on the basis of the Medical Dictionary for Regulatory Authorities (MedDRA) terminology. All reported AEs that occurred on or after the Baseline date through the end of study visit were included in the summaries and analysis. If an event occurred prior to the administration of study drug, it was considered medical history and was listed and summarized as such.

Adverse event summaries included the number and percentage of subjects who reported at least one AE and the number of events reported by severity, seriousness, and relationship to study medication. The summary of adverse events was also presented by system organ class (SOC) and preferred terms (PT) based on MEDDRA version 15.1. A subject was counted only once under each SOC and PT.

Adverse event SOCs and PTs were summarized by severity and relationship to investigational product. For the summary by severity, subjects were only counted once for a specific SOC or PT under the worst severity. Severity was collected as mild, moderate, severe, or life-threatening. For the summary by relationship to investigational product, subjects were only counted once for a specific SOC or PT under the highest relationship. Relationship was collected as definite, probable, possible, unlikely, unrelated, or not applicable. For the summary of relationship, definite, probable, and possible were considered related and unlikely, unrelated, and not applicable was considered unrelated.

All information pertaining to AEs noted during the study were listed by subject, detailing verbatim given by the Investigator, preferred term, system organ class, start date, stop date, severity, seriousness, and relationship to investigational product. The AE onset was also shown relative (in number of days) to the day of initial dose of the randomized investigational product. A summary of adverse events that lead to a subject's discontinuation of investigational product usage was also provided.

P. acnes Counts:

Quantitative bacteriologic cultures were obtained from the forehead at Baseline and at Weeks 2 and 4/ET. Samples were obtained according to a modification of the technique of Williamson and Kligman and cultured for 7 days (Williamson 1965). Colony forming units (cfu) of P. acnes were counted at the dilution that contained between 10 and 100 cfu. Total densities of P. acnes were calculated and reported as log 10 cfu per $cm^2$.

Descriptive statistics of P. acnes, change from baseline, and percent change from baseline were summarized with mean, median, standard deviation, minimum, maximum and 95% confidence intervals. The percent reduction from baseline at Week 2 and Week 4 were calculated using the following formula:

$$\frac{(1 \times 10^X) - (1 \times 10^Y)}{(1 \times 10^X)}$$

Where X=the initial Log value, and Y=the final Log value.

Safety & Tolerability:

In this study, Nitricil™ NVN1 Topical Gel was demonstrated to be safe and well-tolerated. The majority of subjects in the Nitricil™ NVN1 Topical Gel and Vehicle Gel treatment groups did not experience erythema, scaling, dryness, pruritus, or burning/stinging during the treatment period. Scores other than none were generally mild with 1 subject reporting moderate erythema.

A total of 17 AEs were reported by 12 subjects in the Nitricil™ NVN1 Topical Gel treatment groups and 4 AEs were reported by 4 subjects (27%) in the Vehicle Gel treatment group. The most frequent reported AEs were nasal congestion and headache. All AEs were mild or moderate in severity, were judged by the investigator to be unrelated to study medication, required no action to be taken with respect to study medication, and were resolved at the end of the study. No AEs were serious.

For the Nitricil™ NVN1 Topical Gel treatment groups, the methemoglobin level averaged 0.77-0.91% at Baseline, 0.73-0.97% at Week 2, and 0.67-0.85% at Week 4. For the Vehicle Gel treatment group, the methemoglobin level averaged 0.77, 0.91, and 0.83% at Baseline, Week 2, and Week 4, respectively. The highest methemoglobin observed (1.9%) during the study was in a subject treated with Vehicle Gel.

P. acnes Counts:

There was no difference in P. acnes counts in Nitricil™ NVN1 treated subjects versus Topical Gel Vehicle treated groups. The average reduction in P. acnes between Baseline and Week 4 was: 57% (Gel Vehicle); 58% (2% Nitricil™ NVN1); 54% (4% Nitricil™ NVN1); and 63% (8% Nitricil™ NVN1).

Nitricil™ NVN1 was safe and well-tolerated in this study. There were no differences found between treatment groups in tolerability, reported adverse events, laboratory results including methemoglobin concentrations, or physical examinations including vital signs. There was no difference in percent reduction in P. acnes counts from baseline at Week 2 and Week 4 between Nitricil™ NVN1 Topical Gel treated groups and Topical Gel Vehicle.

Example 5

This study was a phase 1, single-center, evaluator-blind, randomized, parallel group, safety and cutaneous tolerability study conducted in 30 healthy volunteers with elevated *Propionobacterium acnes* counts. The objectives of the study were to evaluate the safety and cutaneous tolerability of Nitricil™ NVN1 Gel.

Subjects who satisfied the entry criteria at the Screening and Baseline visits were randomized to 4% Nitricil™ NVN1 Gel or Vehicle Gel in a 2:1 ratio (Table 12). Subjects returned once daily to apply the assigned treatment under supervision. Approximately 1 g was applied over the entire face (3-4% total body surface area (TBSA)), sparing the eyes and mouth, twice daily.

TABLE 12

Test article (4% Nitricil ™ NVN1 Gel) and reference (Vehicle Gel) formulations in a dual chamber pump.

| Ingredient | Nitricil ™ NVN1 4% Gel (% w/w) | Vehicle Gel (% w/w) |
| --- | --- | --- |
| Chamber A | | |
| Isopropyl alcohol | 39.25 | 42.725 |
| Hexylene glycol | 5.00 | 5.00x[1] |
| Cyclomethicone | 1.25 | 1.25x |
| Hydroxylpropyl cellulose | 0.50 | 1.00x |
| Nitricil ™ NVN1 | 4.00 | 0 |
| Titanium dioxide (Opacifier) | 0 | 0.025 |
| Chamber B | | |
| Purified Water | 42.50 | 42.50x |
| Glycerin | 5.00 | 5.00x |
| Carbomer Homopolymer Type C Carbopol ® 980 | 0.50 | 0.50x |
| Citric Acid, anhydrous | 0.05 | 0.05x |
| Benzoic Acid | 0.05 | 0.05x |
| Sorbic Acid | 0.05 | 0.05x |
| Trolamine | QS[1] | QS[2] |
| Purified Water | QS[2] | QS[3] |
| Total | 100.0 | 100.0 |

[1]"x" denotes a non-significant digit.
[2]Quantity sufficient to pH 4 for Chamber B.
[3]Quantity sufficient to make total.

Assessments included cutaneous tolerability, methemoglobin and hemoglobin analysis, physical exams including vital signs, and adverse event collection.

P. acnes cultures from the central forehead were collected at Baseline and post-treatment (Weeks 1 and 2). Subjects returned for post-Baseline evaluation at Week 1 and Week 2/Early Termination (ET).

The diagnosis and main criteria for inclusion were healthy male and female volunteers 18 years of age and older with elevated *P. acnes* counts on the face as demonstrated by a high degree of fluorescence of the facial skin under a Wood's lamp Tolerability and safety assessments included cutaneous tolerability evaluation, adverse events (AEs), hemoglobin and methemoglobin measurements, and physical examination including vital signs.

*P. acnes* cultures were collected from the central forehead via a swab technique at Baseline (BL), Week 1 and Week 2/ET (Williamson 1965).

This was a preliminary study and was not powered for statistical significance. However, the sample size is sufficiently large enough to detect an average 0.75 difference in scores between treatment groups in any of the cutaneous tolerability assessments with 80% power at alpha=0.05. All statistical processing was performed using SAS® unless otherwise stated. Statistical significance was based on two-tailed tests of the null hypothesis resulting in p-values of 0.05 or less, unless otherwise specified. Safety analyses was performed using the safety population.

Cutaneous tolerability assessments (erythema, scaling, dryness, pruritus, burning/stinging) were summarized with frequency counts and percentages at each evaluation for each score category at Week 1 and Week 2. Comparison of treatment differences in distribution of scores was performed using Cochran-Mantel-Haenszel (CMH) chi-square test with MODRIDIT option for ordered scores.

Total hemoglobin was reported; methemoglobin was reported as a percentage of hemoglobin. Hemoglobin and methemoglobin were summarized descriptively by treatment group at Screening and Weeks 1 and 2 and include n, mean, median, standard deviation, minimum, and maximum. Additionally, the change from baseline in hemoglobin and methemoglobin at Weeks 1 and 2 were summarized. Comparison of treatment differences in changes from baseline hemoglobin and methemoglobin were performed using Wilcoxon Rank Sum test.

Quantitative bacteriologic cultures were obtained from the forehead at Baseline and at Weeks 1 and 2. Samples were obtained according to a modification of the technique of Williamson and Kligman and cultured for 7 days (Williamson, B. A.; Kligman, A. M. A new method for the quantitative investigation of cutaneous bacteria. *J. Invest. Dermatol.* 1965, 45, 498-503). Colony forming units (cfu) of *P. acnes* were counted at the dilution that contained between 10 and 100 cfu. Total densities of *P. acnes* were calculated and reported as $\log_{10}$ cfu per $cm^2$.

Descriptive statistics of *P. acnes*, change from Baseline, and percent change from Baseline were summarized with mean, median, standard deviation, minimum, maximum and 95% confidence intervals.

The percent reduction from Baseline at Week 1 and Week 2 were calculated using the following formula:

$$\frac{(1 \times 10^X) - (1 \times 10^Y)}{(1 \times 10^X)}$$

Where X=the initial Log value, and Y=the final Log value.

In this study, Nitricil™ NVN1 4% Gel was demonstrated to be safe and well-tolerated. The majority of subjects in Nitricil™ NVN1 4% Gel and Vehicle Gel treatment groups did not experience erythema, scaling, dryness, pruritus, or burning/stinging during the treatment period.

No adverse events were reported in this study. No clinically significant change in blood pressure, pulse or findings on physical exam were seen between Baseline and the end of treatment. No clinically significant changes in percent methemoglobin or hemoglobin concentration were found.

After 1 week of treatment, there was a mean logarithm reduction in *P. acnes* counts of 0.38 for the Nitricil™ NVN1 4% Gel group compared to 0.20 for the Vehicle Gel group. After 2 weeks, subjects treated with Nitricil™ NVN1 4% Gel had a mean reduction in *P. acnes* counts of 0.51 $\log_{10}$ cfu per $cm^2$ compared to 0.26 $\log_{10}$ cfu per $cm^2$ for the subjects treated with Vehicle Gel. The difference at Week 2 was statistically significant, p=0.04, using a Student's T-Test. A post-hoc ANCOVA also demonstrated a statistically significant difference in *P. acnes* reduction in subjects treated with Nitricil™ NVN1 4% Gel and Vehicle Gel, p=0.03.

Nitricil™ NVN1 4% Gel was safe and well-tolerated in this study. There was a statistically significant difference between Nitricil™ NVN1 4% Gel treated groups and Vehicle Gel treated groups in the percent reduction in *P. acnes* counts.

Example 6

The primary objective of this study was to evaluate the cutaneous tolerability of Nitricil™ NVN1 4% Gel (containing a hydrogel) at Baseline and Weeks 1 and 2/ET. The secondary objective was to evaluate the safety profile of Nitricil™ NVN1 Gel. Safety was assessed by comparing adverse events between groups (including clinically significant changes in physical exams and vital signs), changes in hemoglobin and the percent methemoglobin. Exploratory analysis of efficacy as measured by reduction of *P. acnes* as determined by changes in the number of organisms from cultures at the Baseline Visit, Week 1 and Week 2/ET was performed.

The study panel had 30 subjects who were healthy adult males and females 18 years of age and older and who were colonized by *P. acnes*. Subjects were carefully screened to ensure that none were using any prohibited topical or systemic antibiotics within 4 weeks prior to enrollment. The panelists were instructed not to use any medicated shampoos. The volunteers selected for the study showed a high degree of fluorescence of the facial skin under a Wood's lamp indicating the presence of high levels of *P. acnes*. Baseline *P. acnes* counts were at least 10,000 colonies per $cm^2$ on the facial skin.

All subjects met the below inclusion/exclusion criteria.

Inclusion Criteria:
 Have a signed written informed consent form.
 Be a healthy, adult male or female volunteer, 18 years of age and older.
 Show a high degree of fluorescence of the facial skin under a Wood's lamp indicating the presence of high levels of *P. acnes*.
 Have no past or present history of any significant internal disease (e.g. cardiovascular, pulmonary, renal, etc.).
 If a woman of childbearing potential (WOCBP), have a negative urine pregnancy test (UPT) at Baseline.
 If a WOCBP, agree to use an effective method of birth control during the course of the study and for 30 days after the final study visit. Females taking hormonal contraceptives must have taken the same type for at least three months (90 days) prior to entering the study and must not change type during the study. Those who have used hormonal contraceptives in the past and stopped must have discontinued usage at least three months prior to the start of the study.

Agree to refrain from using antimicrobial topical products (shampoos, soaps, acne preparations, etc.).

Be compliant and able to return to site as instructed once daily (Monday-Friday) for approximately two weeks.

Exclusion Criteria:

Subjects were not enrolled if they met any of the following exclusion criteria:

Exhibit any skin disorders of an acute or chronic nature including psoriasis, eczema, etc.

Have a history of experiencing significant burning or stinging when applying any facial treatment (e.g., make-up, soap, masks, washes, sunscreens, etc.) to their face.

Female subjects who are pregnant, nursing mothers, or planning to become pregnant during the study.

Male subjects who do not agree to sexual abstinence, refraining from sperm donation and/or using a barrier (male condom) throughout the study.

Have used estrogens (e.g., Depogen, Depo-Testadiol, Gynogen, Valergen, etc.) or oral contraceptives for less than 90 days immediately preceding the Baseline visit, discontinued use of estrogens or oral contraceptives less than 90 days prior to Baseline, or planning to begin or discontinue use of this therapy during the treatment period.

Have used topical or systemic antibiotics within the previous 4 weeks that are known to influence P. acnes counts e.g. minocycline, tetracycline, erythromycin, clindamycin, doxycycline etc.

Use of other medications which may influence skin surface P. acnes levels (e.g., retinoids) within the previous 6 months.

Use nitroglycerin or other nitric oxide donor drug concomitantly.

Have a clinically significant anemia (as determined by the principal investigator) at Baseline.

Have a Screening methemoglobin value of ≥2.0%.

Have clinically significant anemia at Screening as determined by the Investigator.

Are known to be allergic to any of the components in the investigational product.

Have intercurrent illness requiring administration of prohibited antibiotics.

Have any condition or situation which, in the Investigator's opinion, puts the subject at significant risk, could confound the study results, or may interfere significantly with the subject's participation in the study. Subjects undergoing endoscopy with use of topical anesthetics should not be enrolled in and should be discontinued from the study prior to endoscopy. Subjects with clinically significant anemia, as determined by the Investigator, should not be enrolled.

Are unable to communicate or cooperate with the Investigator due to language problems, poor mental development, or impaired cerebral function.

Have used an investigational drug or device within 30 days of enrollment or concurrent participation in a different research study.

Volunteers were free to withdraw their consent and discontinue participation in the study at any time.

Candidates were screened for eligibility prior to enrollment. After ensuring qualification and signing an informed consent, quantitative Baseline measurements of P. acnes (on the forehead) were obtained (see section below "Quantitative Bacteriology").

Treatment Plan:

Treatment was for two weeks. Each weekday morning under supervision by a technician at the Skin Study Center, the volunteer washed their face and then applied the test product. Approximately 1 g of Nitricil™ NVN1 4% Gel or Gel Vehicle (Table 12) was applied evenly over the entire face (4% TBSA), sparing the eyes and mouth. The investigational product was dispensed from a dual chamber pump by depressing the pump 3 times. The dispensed material was quickly (3-5 seconds) mixed together and applied in a thin layer to the face, sparing the eyes and mouth. The product was then gently massaged into the skin for about 30 seconds. Subjects washed their hands after study drug application. This procedure of washing the face, applying the test product and then washing of hands was done in the evening by the panelists at home (no supervision).

All treatments were documented on the Subject Diary.

Quantitative Bacteriology:

Quantitative bacteriologic cultures were obtained from the test sites at Baseline (0) and at Weeks 1 and 2. Samples were obtained according to a modification of the technique of Williamson and Kligman (Williamson, P. and Kligman, A. M.: A new method for the quantitative investigation of cutaneous bacteria. Journal of Investigative Dermatology 45: 498-503, 1965; Keyworth N., Millar, M. R., and Holland, K. T.: Swab-Wash Method for Quantitation of Cutaneous Microflora. J. Clin. Microbiology, Vol. 28, pp. 941-943, 1990). The forehead was cleansed of surface bacteria by thoroughly wiping the area for 30 seconds with sterile gauze soaked with 0.1% Triton-X-100 to remove surface debris and bacteria. The surface area to be cultured (4 cm2) was then delineated by a sterile plastic template held firmly to the skin. A sterile cotton-tipped swab was dipped into 2 ml of wash solution (Bacto Letheen Broth, Difco, Sparks, Md., USA). The area was then scrubbed with the cotton-tipped swab for 30 seconds. The swab was then placed back into the 2 ml wash solution and wrung on the side of the tube. The same skin area was then scrubbed again for another 30 seconds after which the cotton-tipped swab is again placed back into the 2 ml of wash solution and wrung on the side of the tube. The swab was then broken off into the 2 ml of wash solution. The sample was subsequently processed as described in the Williamson-Kligman method viz. the wash sample was serially diluted using 0.05% Tween-80 (buffered with 0.075M phosphate buffer, pH 7.9) in 4 ten-fold dilutions. Using a micropipettor, 0.05 mL of each dilution was placed on a designated section of an agar plate containing Brucella agar supplemented with yeast extract, dextrose, and cysteine, five drop dilutions per plate. Duplicate plates were made for each subject. Plates were allowed to dry, placed in an anaerobic jar with BBL Gas Pak Plus anaerobic system envelope and incubated anaerobically at 36.5-37.50 C for 7 days. Colony forming units (cfu) of P. acnes are counted at the dilution that contains between 10 and 100 cfu. Total densities of P. acnes were calculated and reported as $\log_{10}$ cfu per $cm^2$.

Cutaneous Tolerability Assessment:

At Baseline, Week 1 and Week 2, cutaneous tolerability assessments were made by the dermatologist prior to treatment. Cutaneous tolerability endpoints were not reported as an AE unless they reached severe and/or result in subject's discontinuation from the study. Cutaneous tolerability assessments were performed according to the following scales:

Erythema

0-None No evidence of erythema present

1-Mild Slight pink coloration

2-Moderate Definite redness

3-Severe Marked erythema, bright red to dusky dark red in color

Scaling

0-None No scaling

1-Mild Fine scales present to limited areas of the face, barely perceptible

2-Moderate Fine scale generalized to all areas of the face

3-Severe Scaling and peeling of skin over all areas of the face

Dryness

0-None No dryness

1-Mild Slight but definite roughness

2-Moderate Moderate roughness

3-Severe Marked roughness

Pruritus

0-None No itching

1-Mild Slight itching, not very bothersome

2-Moderate Moderate amount of itching, somewhat bothersome

3-Severe Severe amount of itching, definite discomfort and sleep may be disturbed Burning/Stinging 0-None No burning/stinging 1-Mild Slight warm, burning/stinging sensation; not very bothersome 2-Moderate Definite warm, burning/stinging sensation that is somewhat bothersome 3-Severe Hot, tingling/sensation that has caused definite discomfort and may have disturbed sleep Laboratory Assessments:

Hemoglobin was measured at Baseline and at Weeks 1 and 2/ET using a Masimo Rainbow® SET® Rad57™ pulse co-oximeter. The amount of hemoglobin (g/dL) was displayed on the pulse co-oximeter and recorded on the CRF.

Methemoglobin was measured at Baseline and at Weeks 1 and 2/ET using a Masimo Rainbow® SET® Rad-57™ pulse co-oximeter. The percent methemoglobin was displayed on the pulse co-oximeter and recorded on the CRF.

All WOCBP had a urine pregnancy test (UPT) at Baseline and at their final evaluation visit (Week 2/ET).

A brief physical exam was performed at Baseline and Week 2/ET.

Systolic and diastolic blood pressure and pulse were collected at Baseline and Weeks 1 and 2/ET.

Data Processing:

Cultures were plated in duplicate with tenfold dilutions from 100 to 104. Bacterial counts were obtained from the dilution at which colony forming units (CFUs) are significantly dispersed and then converted to total number per sq. cm. The raw data for each plate and the average was provided in separate columns. Sorting templates were based on Excel 2007 spreadsheet software. The sorted data for each session were tabulated.

Data analysis involved a Paired T-Test to comparing Baseline means with treatment points. A Student's T-Test was used to compare means for the two treatments. A two tailed p<0.05 is required for a significant difference.

Thirty-three (33) panelists were screened for this study and a total of thirty (30) panelists were enrolled. Twenty-nine (29) panelists completed. One panelist withdrew consent from the study due to redness after application. There were no adverse events.

No erythema or scaling was observed by the dermatologist during the course of this study. Minimal dryness, pruritus and burning or stinging was noted as follows.

Three subjects using Nitricil™ NVN1 4% Gel (Treatment A) reported dryness at Week 2. Two subjects using Treatment A reported pruritus at Week 1. At week 1, one subject reported burning/stinging using Treatment A.

In this trial, the cutaneous tolerability and systemic safety of a 4% Nitricil™ NVN1 gel formulation was evaluated after 1 and 2 weeks of B.I.D. treatment. In addition, an exploratory analysis of in-vivo reduction of *Propionibacterium acnes*, the organism responsibility for the inflammation in acne vulgaris, was done after 1 and 2 weeks of treatment. The test panel consisted of 30 healthy volunteers with *P. acnes* levels of $10^4/cm^2$ or greater; 20 were treated with the active agent and 10 with the vehicle.

The test agent and its vehicle were extremely well tolerated. No objective signs of irritation and no subjective symptoms of pruritus, burning or stinging were seen except for moderate pruritus in 1 panelist and mild in another panelist at the Week 1 visit. Mild burning/stinging was reported by one panelist at Week 1. Mild dryness was seen in 3 panelists at Week 2. One panelist withdrew on Day 1 because of concerns about the physiological vasodilatation induced by the test agent. No sign of irritation was seen in this panelist.

No clinically significant change in blood pressure, pulse or findings on physical exam were seen between Baseline and the end of treatment. No clinically significant changes in percent methemoglobin or hemoglobin concentration were found.

After 1 week of treatment, there was a mean logarithm reduction of 0.38 for the active agent compared to 0.20 for the vehicle. After 2 weeks, the active agent had a mean reduction of 0.51 compared to 0.26 for the vehicle. The difference at Week 2 was statistically significant using a student's T-test (p=0.04). The response was variable in test agent with 2 panelists showing greater than 1 log reduction after 2 weeks of treatment, 5 others with 0.5 or greater but less than 1 log reduction and 3 panelists showing less than the mean reduction in the vehicle group.

Figure 9:
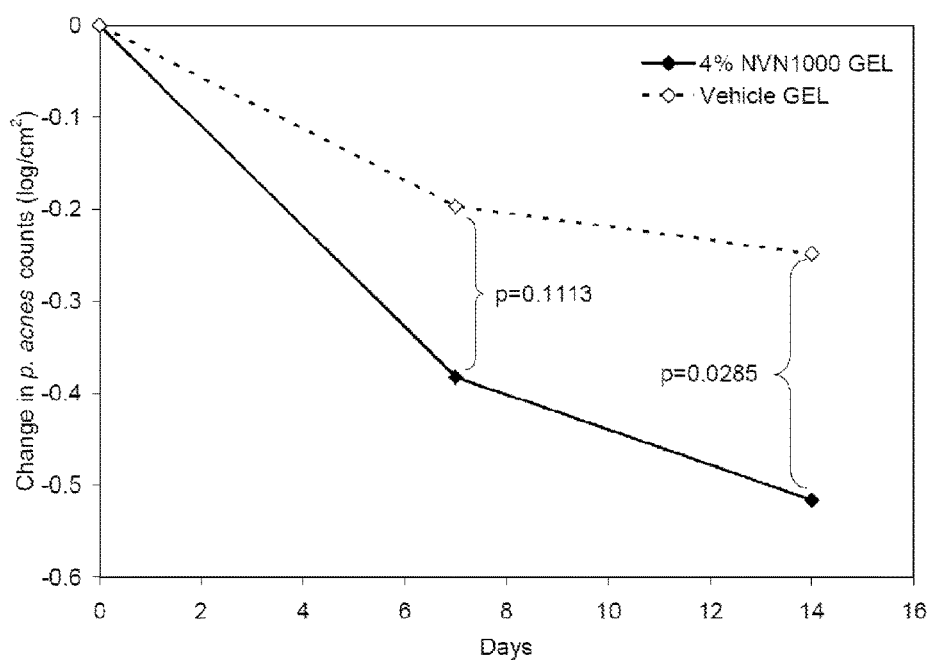
FIG. 9 shows a graph of the change in P. acnes counts ($log/cm^2$) over time based on an analysis of co-variance (ANCOVA).

An analysis of co-variance (ANCOVA) demonstrated statistically significant differences in for *P. acnes* counts at week 1 and week 2 (FIG. 9).

The test agent and its vehicle were well tolerated and showed no signs of cutaneous or systemic toxicity. A variable in-vivo antibacterial effect in *P. acnes* was seen which may be of benefit in acne therapy.

Example 7

This study was a multi-center, randomized, evaluator-blinded, vehicle-controlled, parallel group, three-arm study to compare the efficacy, safety, and tolerability of two concentrations of Nitricil™ NVN1 Gel and Vehicle Gel in subjects with acne vulgaris treated for 12 weeks. Subjects who met the study entry criteria were enrolled and randomized to receive topical applications of Nitricil™ NVN1 1% Gel, Nitricil™ NVN1 4% Gel, or Vehicle Gel (Table 13). Subjects were randomized in a 1:1:1 ratio to Nitricil™ NVN1 1% Gel, Nitricil™ NVN1 4% Gel, or Vehicle Gel and instructed to dose twice daily (morning and night) for 12 weeks (84 days). The first application of study drug took place at the investigational site at the Baseline visit.

TABLE 13

Test article (Nitricil ™ NVN1 1% Gel and Nitricil ™ NVN1 4% Gel) and reference (Vehicle Gel) formulations in a dual chamber pump.

| Ingredient | Nitricil ™ NVN1 1% Gel (% w/w) | Nitricil ™ NVN1 4% Gel (% w/w) | Vehicle Gel (% w/w) |
|---|---|---|---|
| Chamber A | | | |
| Isopropyl alcohol | 41.75 | 39.25 | 42.725 |
| Hexylene glycol | 5.00 | 5.00 | 5.00x[1] |
| Cyclomethicone | 1.25 | 1.25 | 1.25x |
| Hydroxylpropyl cellulose | 1.00 | 0.50 | 1.00x |
| Nitricil ™ NVN1 | 1.00 | 4.00 | 0 |
| Titanium dioxide (Opacifier) | 0 | 0 | 0.025 |
| Chamber B | | | |
| Purified Water | 42.50 | 42.50 | 42.50x |
| Glycerin | 5.00 | 5.00 | 5.00x |
| Carbomer Homopolymer Type C Carbopol ® 980 | 0.50 | 0.50 | 0.50x |
| Citric Acid, anhydrous | 0.05 | 0.05 | 0.05x |
| Benzoic Acid | 0.05 | 0.05 | 0.05x |
| Sorbic Acid | 0.05 | 0.05 | 0.05x |
| Trolamine | QS[1] | QS[1] | QS[2] |
| Purified Water | QS[2] | QS[2] | QS[3] |
| Total | 100.0 | 100.0 | 100.0 |

[1] "x" denotes a non-significant digit.
[2] Quantity sufficient to pH 4 for Chamber B.
[3] Quantity sufficient to make total.

After the Baseline visit, study visits took place approximately every two weeks for the first four weeks, then every four weeks for the next eight weeks. The study duration was up to 84 days of treatment.

Efficacy assessments included inflammatory (papules and pustules) and noninflammatory (open and closed comedones) lesion counts, nodules and cysts counts, and Investigator's Global Assessment (IGA), which were performed at Baseline and Weeks 4, 8, and 12/Early Termination (ET).

Additional assessments included photographs and sebum collection. Photographs were collected at Baseline, Week 4 and Week 12/ET. Sebum was collected from the central forehead of subjects enrolled at two investigational sites at Baseline, Week 4, and Week 12/ET using Sebutapes®.

Tolerability and safety assessments included cutaneous tolerability evaluation, adverse event (AE) collection, physical exams including blood pressure and pulse rate, methemoglobin and hemoglobin measurements, and urine pregnancy tests (UPTs). Cutaneous tolerability assessments (erythema, scaling, dryness, pruritus, and burning/stinging) were evaluated prior to and 30 minutes after the first application of study drug at the Baseline visit and at each subsequent visit. The cutaneous tolerability assessments for visits other than the Baseline were to be performed at least 30 minutes after study drug application. AEs were collected starting after the subject had signed the informed consent and completed any study assessment until the end of the final study visit. A brief physical exam was performed at Baseline (Visit 1/Day 0) and Week 12/ET. Blood pressure and pulse rate were collected pre-dose at Baseline and at Weeks 2, 4, 8, and 12/ET. Methemoglobin and hemoglobin were measured at Baseline, Week 2 and Week 12/ET using a Masimo Rainbow® SET® Rad57™ pulse co-oximeter that analyzed methemoglobin and hemoglobin levels. Subjects with methemoglobin values of >2.0 percent at Baseline and subjects with clinically significant anemia at Baseline were not eligible to participate in the study. All women of child-bearing potential (WOCBP) must have had a UPT at Baseline and if the result was positive, the subject was not allowed to participate in the study. WOCBP also were to have a UPT at Weeks 4, 8, and 12/ET. Subjects who terminated early were asked to complete all Week 12/ET evaluations at the time of premature discontinuation.

The number of subjects in the intent to treat population were: 52 subjects for the Vehicle Gel group, 51 subjects for the Nitricil™ NVN1 1% Gel group, and 50 subjects for the Nitricil™ NVN1 4% Gel group. However, not all of the subjects completed the study, and thus 45 subjects completed the study for the Vehicle Gel group, 43 subjects completed the study for the Nitricil™ NVN1 1% Gel group, and 41 subjects completed the study for the Nitricil™ NVN1 4% Gel group.

The study included healthy males and females of any race who were 12 to 40 years of age (inclusive), with acne vulgaris. Subjects must have had at least 20 but no more than 40 inflammatory lesions (papules and pustules), 25 to 70 noninflammatory lesions (open and closed comedones), no more than two nodules, and investigator's global assessment (IGA) of 2, 3, or 4.

The Nitricil™ NVN1 1% Gel, Nitricil™ NVN1 4% Gel, and Vehicle Gel were administered by applying approximately 1 gram evenly over the entire face twice a day (morning and evening). The active gel (Chamber A) and hydrogel (Chamber B) were dispensed concurrently from a dual chamber pump in a ratio of 1:1 and mixed by the subject immediately prior to application. The Vehicle Gel (Chamber A) and hydrogel (Chamber B) were dispensed concurrently from a dual chamber pump and mixed by the subject immediately prior to application.

At Baseline and Weeks 4, 8, and 12/ET, the investigator counted the total number of noninflammatory lesions on the subject's face including the forehead, right and left cheeks, chin and nose. At Baseline and Weeks 4, 8, and 12/ET, the investigator also counted the total number of inflammatory lesions on the subject's face, including the forehead, right and left cheeks, nose, and chin. The lesion count for the nose (inflammatory and noninflammatory) and the number of nodules and cysts were reported separately, but for analyses, the inflammatory lesion count included the collective number of papules, pustules, and nodules/cysts.

The IGA was performed at Baseline and Weeks 4, 8, and 12/ET. The IGA score was determined based on the investigator evaluation of the overall signs and symptoms of acne vulgaris. Evaluations were scored on a scale of 0 (clear) to 4 (severe).

Photographs were collected at Baseline, Week 4 and Week 12/ET.

Sebum was collected from the central forehead of subjects enrolled at two investigational sites at Baseline, Week 4, and Week 12/ET using Sebutapes®.

The investigator evaluated the subject's face prior to and 30 minutes after the first application of investigational product in addition to evaluating at each study visit. The cutaneous tolerability assessment for visits other than the Baseline should have been performed at least 30 minutes after study drug application. Cutaneous tolerability evaluations included erythema, scaling, dryness, pruritus, and burning/stinging.

Methemoglobin and hemoglobin were measured at Baseline, Week 2 and Week 12 using a Masimo Rainbow® SET® Rad-57™ pulse co-oximeter that analyzed methemoglobin and hemoglobin levels.

A brief physical exam was performed at Baseline (Visit 1/Day 0) and Week 12/ET. Blood pressure and pulse rate were collected pre-dose at Baseline and at Weeks 2, 4, 8, and 12/ET. The investigator assessed subjects at each scheduled study visit for the occurrence of AEs.

The primary efficacy endpoint was absolute change from baseline in non-inflammatory lesion count on the face including the nose at Week 12.

Analysis of the primary endpoint of absolute change in non-inflammatory lesion count on the face including the nose at Week 12 was conducted using an analysis of covariance (ANCOVA) with factors of treatment and investigational site and baseline lesion count as a covariate. A linear regression also was performed to determine dose response where the slope (β) was estimated across treatments (1% and 4%) and where the Vehicle Gel was labeled as 0% for the regression. The null test was that (β=0 versus the alternative that β is not equal 0. Rejection of the null hypothesis with a positive β indicated a dose response.

Secondary efficacy endpoints were: Absolute change from baseline in inflammatory lesion count at Week 12, absolute change from baseline in non-inflammatory lesion count on the face excluding the nose at Week 12, and dichotomized IGA at Week 12.

Inflammatory lesion count included the collective number of papules, pustules, and nodules/cysts.

The analysis of the absolute change in inflammatory lesion counts at Week 12 used the same methods outlined for the primary efficacy analysis of change in noninflammatory lesion counts including the nose.

The analysis of the absolute noninflammatory lesion count on the face excluding the nose at Week 12 used the same methods outlined for the primary efficacy analysis of change in noninflammatory lesion counts on the face including the nose.

The dichotomized IGA scores at Week 12 were analyzed using a logistic regression model where treatment and investigational sites were the independent factors. The dichotomized IGA score was relabeled as 0 for failure and 1 for success as the dependent variable in the logistic regression. Success was defined as a score of 'clear' (0) or 'almost clear' (1) with at least a two-grade improvement from baseline. Additionally, treatment groups were compared using the Cochran-Mantel-Haenszel (CMH) test stratified by investigational site. Pairwise comparisons were computed without concern for controlling for multiplicity.

Cutaneous tolerability assessments (erythema, scaling, dryness, pruritus, and burning/stinging) were summarized as frequency counts and percentages at each evaluation. Methemoglobin was reported as a percentage of hemoglobin. Total hemoglobin also was reported. Methemoglobin and hemoglobin were summarized descriptively by treatment group at Baseline and Weeks 2 and 12 and included sample size, mean, median, standard deviation (SD), minimum, and maximum. Additionally, the changes from baseline in methemoglobin and hemoglobin at Weeks 2 and 12 were summarized.

Summaries were presented to describe the characteristics of the AEs reported and included the number and percentage of subjects who reported at least one AE and the number of events reported by severity, seriousness, and relationship to study drug.

Blood pressure and pulse rate were summarized at Baseline, Week 2, Week 4, Week 8, and Week 12/ET as well as the change from Baseline at Week 12/ET by treatment group with mean, SD, minimum, and maximum.

For the ITT population, the Nitricil™ NVN1 1% Gel and Nitricil™ NVN1 4% Gel LSMean changes from baseline for absolute noninflammatory lesions (including and excluding the nose) were statistically significantly larger decreases than the corresponding Vehicle Gel LSMean changes from baseline for absolute noninflammatory lesions (including and excluding the nose), but linear dose responses were not seen. The Nitricil™ NVN1 4% Gel LSMean change from baseline for absolute inflammatory lesions was a statistically significantly larger decrease than the Vehicle Gel LSMean change from baseline for absolute inflammatory lesions, but the Nitricil™ NVN1 1% Gel LSMean change from baseline for absolute inflammatory lesions was not statistically different from the Vehicle Gel LSMean change from baseline for absolute inflammatory lesions. A linear dose response was seen. No differences were seen among treatment groups for the dichotomized IGA. Specifically, The LSMean absolute change from baseline for noninflammatory lesions (including nose) was −11.8 lesions for the Nitricil™ NVN1 1% Gel group compared to −0.7 lesions for the Vehicle Gel group (p=0.022). The LSMean absolute change from baseline for noninflammatory lesions (including nose) was −11.1 lesions for the Nitricil™ NVN1 4% Gel group compared to −0.7 lesions for the Vehicle Gel group (p=0.031). A linear dose response was not seen among the treatment groups (p=0.105). The LSMean absolute change from baseline for inflammatory lesions was −13.8 lesions for the Nitricil™ NVN1 1% Gel group compared to −9.4 lesions for the Vehicle Gel group (p=0.088). The LSMean absolute change from baseline for inflammatory lesions was −15.5 lesions for the Nitricil™ NVN1 4% Gel group compared to −9.4 lesions for the Vehicle Gel group (p=0.018). A linear dose response was seen among the treatment groups (p=0.033).

The LSMean absolute change from baseline for noninflammatory lesions (excluding nose) was −10.9 lesions for the Nitricil™ NVN1 1% Gel group compared to −1.3 lesions for the Vehicle Gel group (p=0.032). The LSMean absolute change from baseline for noninflammatory lesions (excluding nose) was −10.6 lesions for the Nitricil™ NVN1 4% Gel group compared to −1.3 lesions for the Vehicle Gel group (p=0.039). A linear dose response was not seen among the treatment groups (p=0.118).

0.0% (0/51) subjects were characterized as success for the dichotomized IGA for the Nitricil™ NVN1 1% Gel group compared to 19% (1/52) subjects for the Vehicle Gel group (p≥0.317). 2.0% (1/50) subjects were characterized as success for the dichotomized IGA for the Nitricil™ NVN1 4% Gel group compared to 1.9% (1/52) subjects for the Vehicle Gel group (p>0.601).

For the Safety population, Nitricil™ NVN1 1% Gel and Nitricil™ NVN1 4% Gel were safe and generally well tolerated. There were no serious adverse events and the Nitricil™ NVN1 1% Gel and Nitricil™ NVN1 4% Gel showed good cutaneous tolerability. A review of the methemoglobin and hemoglobin results did not identify any safety signals. A review of the vital signs results did not identify any safety signals.

Figure 10:
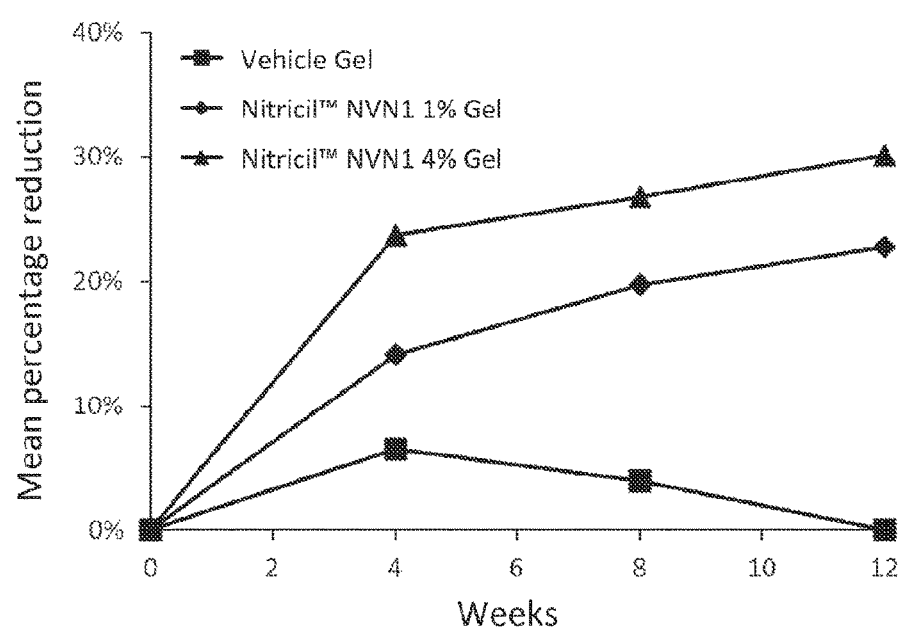
FIG. 10 shows a graph of the mean percentage reduction over time for noninflammatory lesions in the per-protocol population.

For the PP population, Nitricil™ NVN1 1% Gel and Nitricil™ NVN1 4% Gel both demonstrated a mean percentage reduction for noninflammatory lesions over time compared to the Vehicle Gel (FIG. 10). FIG. 10 shows that separation from the Vehicle Gel group occurred at week 4 for both the Nitricil™ NVN1 1% Gel and Nitricil™ NVN1 4% Gel groups. At week 4, the Vehicle Gel group had a 6% mean percentage reduction for noninflammatory lesions, whereas the Nitricil™ NVN1 1% Gel group had a 14% mean percentage reduction for noninflammatory lesions and the Nitricil™ NVN1 4% Gel group had a 24% mean percentage reduction for noninflammatory lesions. The noninflammatory lesion count for the PP population is provided in Table 14.

TABLE 14

Summary of noninflammatory lesion counts (including nose) at each evaluation for the per-protocol population.

| | Baseline | Week 4 | Week 8 | Week 12 |
|---|---|---|---|---|
| Vehicle Gel (N = 46) | | | | |
| Mean | 47.7 | 44.8 | 46.8 | 48.2 |
| SD | 14.17 | 23.77 | 32.83 | 34.97 |
| Median | 47.5 | 40.0 | 36.5 | 40.0 |
| Min. to Max. | 25 to 70 | 10 to 116 | 9 to 152 | 10 to 176 |
| Nitricil ™ NVN1 1% Gel (N = 42) | | | | |
| Mean | 52.5 | 44.3 | 42.1 | 39.9 |
| SD | 13.49 | 18.46 | 29.01 | 20.72 |
| Median | 54.5 | 41.0 | 37.0 | 39.0 |
| Min. to Max. | 29 to 70 | 13 to 89 | 8 to 162 | 10 to 110 |
| Nitricil ™ NVN1 4% Gel (N = 43) | | | | |
| Mean | 51.0 | 40.2 | 38.2 | 37.2 |
| SD | 14.70 | 22.57 | 22.18 | 28.76 |
| Median | 52.0 | 37.0 | 37.0 | 30.0 |
| Min. to Max. | 25 to 70 | 5 to 112 | 4 to 90 | 3 to 131 |

Figure 11:
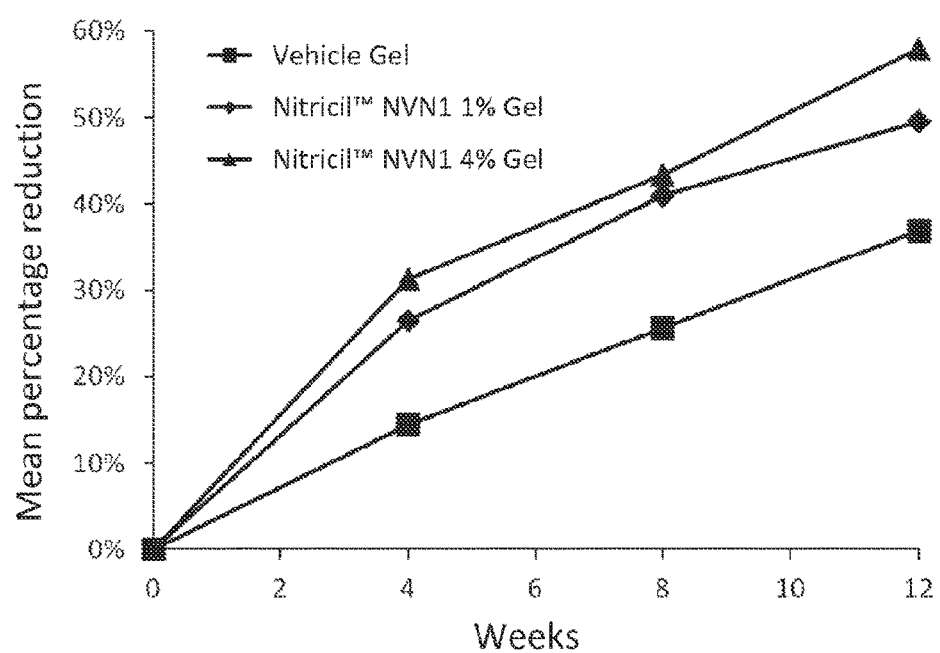
FIG. 11 shows a graph of the mean percentage reduction over time for inflammatory lesions in the per-protocol population.

A mean percentage reduction for inflammatory lesions over time was seen in the PP population for both Nitricil™ NVN1 1% Gel and Nitricil™ NVN1 4% Gel compared to the Vehicle Gel (FIG. 11). FIG. 11 shows that separation from the Vehicle Gel group occurred at week 4 for both the Nitricil™ NVN1 1% Gel and Nitricil™ NVN1 4% Gel groups. At week 4, the Vehicle Gel group had a 14% mean percentage reduction for inflammatory lesions, whereas the Nitricil™ NVN1 1% Gel group had a 26% mean percentage reduction for inflammatory lesions and the Nitricil™ NVN1 4% Gel group had a 31% mean percentage reduction for inflammatory lesions.

For the PP population at week 12, the median percent reduction in inflammatory lesions was as follows: 56% for the Nitricil™ NVN1 1% Gel group, 66% for the Nitricil™ NVN1 4% Gel group, and 42% for the Vehicle Gel group. Thus, the median percent reduction in inflammatory lesions for the PP population was higher than the mean percent reduction in inflammatory lesions for the PP population for each group. For the Nitricil™ NVN1 4% Gel group, 20 of the 41 patients completing the study had a reduction in inflammatory lesions of greater than 70%. The inflammatory lesion count for the PP population is provided in Table 15.

TABLE 15

Summary of inflammatory lesion counts at each evaluation for the per-protocol population.

| | Baseline | Week 4 | Week 8 | Week 12 |
|---|---|---|---|---|
| Vehicle Gel (N = 46) | | | | |
| Mean | 28.9 | 25.6 | 22.1 | 19.2 |
| SD | 6.11 | 20.14 | 21.34 | 20.04 |
| Median | 28.0 | 21.5 | 17.0 | 17.0 |
| Min. to Max. | 20 to 40 | 4 to 127 | 3 to 127 | 0 to 127 |
| Nitricil ™ NVN1 1% Gel (N = 42) | | | | |
| Mean | 29.4 | 21.4 | 17.2 | 14.7 |
| SD | 5.91 | 8.65 | 10.91 | 10.15 |
| Median | 28.0 | 20.5 | 17.0 | 13.5 |
| Min. to Max. | 22 to 42 | 8 to 48 | 0 to 48 | 1 to 48 |

TABLE 15-continued

Summary of inflammatory lesion counts at each evaluation for the per-protocol population.

| | Baseline | Week 4 | Week 8 | Week 12 |
|---|---|---|---|---|
| Nitricil ™ NVN1 4% Gel (N = 43) | | | | |
| Mean | 29.3 | 20.6 | 16.9 | 12.7 |
| SD | 5.00 | 12.20 | 11.19 | 10.10 |
| Median | 29.0 | 18.0 | 15.0 | 10.0 |
| Min. to Max. | 20 to 41 | 4 to 61 | 0 to 54 | 2 to 47 |

Compared to the Vehicle Gel group, the Nitricil™ NVN1 1% Gel group was effective in lowering the number of noninflammatory and inflammatory lesions (including and excluding nose), and the Nitricil™ NVN1 4% Gel group was effective in lowering the number of noninflammatory lesions (including and excluding nose) and inflammatory lesions. The Nitricil™ NVN1 4% Gel group demonstrated statistically significant differences compared to the Vehicle Gel group, and the Nitricil™ NVN1 4% Gel group differed from the Vehicle group on primary and secondary endpoints. Both Nitricil™ NVN1 1% Gel and Nitricil™ NVN1 4% Gel were safe and well tolerated, and no safety signals were identified.

Example 8

Three American Board of Dermatology certified dermatologists with experience in conducting acne clinical studies conducted a post-hoc Investigator's Global Assessment (IGA) analysis based on the study described in Example 7. The purpose of this analysis was to have investigators with experience in conduct of clinical trials for U.S. approval evaluate the results of treatment. The IGA scoring description for Examples 7 and 8 is provided in Table 16. The definition of "success" is a score at end of treatment of "0" (clear) or "1" (almost clear) and a minimum 2 grade change from baseline.

TABLE 16

IGA scoring description used for the study described in Examples 7 and 8.

| Grade | Description |
|---|---|
| 0 | Clear skin with no inflammatory or non-inflammatory lesions. |
| 1 | Almost clear; rare non-inflammatory lesions with no more than one inflammatory lesion. |
| 2 | Mild severity; greater than Grade 1; some non-inflammatory lesions with no more than a few inflammatory lesions (papules/pustules only, no nodular lesions). |
| 3 | Moderate severity; greater than Grade 2; up to many non-inflammatory lesions and may have some inflammatory lesions, but no more than one small nodular lesion |
| 4 | Severe; greater than Grade 3; up to many non-inflammatory and inflammatory lesions, but no more than a few nodular lesions |

The three board-certified dermatologists conducted a blind review of the clinical images available for a subject at both Baseline and Week 12 and "scored" the images taken at Baseline and Week 12. The results are provided in Table 17 below. All three dermatologists judged the Nitricil™ NVN1 Gel, particularly the Nitricil™ NVN1 4% Gel, to have activity in the treatment of acne vulgaris.

TABLE 17

Post-hoc analysis results.

| | Vehicle Gel (N = 44) | Nitricil ™ NVN1 1% Gel (N = 44) | Nitricil ™ NVN1 4% Gel (N = 41) |
|---|---|---|---|
| Dermatologist 1 | | | |
| ≥2 Grade change at end of treatment | 3 (6.8%) | 5 (11.4%) | 12 (29.3%) |
| "Success" | 2 (4.5%) | 3 (6.8%) | 5 (12.2%) |
| Dermatologist 2 | | | |
| ≥2 Grade change at end of treatment | 5 (11.4%) | 4 (9.1%) | 10 (24.4%) |
| "Success" | 1 (2.3%) | 0 (0.0%) | 4 (9.8%) |
| Dermatologist 3 | | | |
| ≥2 Grade change at end of treatment | 5 (11.6%) | 6 (13.6%) | 13 (31.7%) |
| "Success" | 2 (4.7%) | 3 (6.8%) | 5 (12.2%) |

Example 9

Cosmetically elegant compositions comprising benzoyl peroxide were prepared. Each composition contained two parts, one part was a benzoyl peroxide gel containing a carboxypolymethylene and the second part was a composition containing a cellulose. Each part was filled into one chamber of a YonWoo 2×15 mL dual chamber pump. The benzoyl peroxide gel formulations are provided in Tables 18 and 19 and the cellulose composition for separate combination with each of the two benzoyl peroxide gel formulations is provided in Table 20.

TABLE 18

Benzoyl peroxide gel formulation 1.

| Ingredient | % w/w | g/batch (Calculated) |
|---|---|---|
| Water | 35.0 | 175.0 |
| Ethanol, Absolute | 30.0 | 150.0 |
| Hexylene Glycol | 12.0 | 60.0 |
| Benzoyl Peroxide, 75% (Luperox ® A75FP)* | 6.7 | 33.5 |
| Carbopol ® 974P | 1.0 | 5.0 |
| EDTA, Disodium | 0.1 | 0.5 |
| Trolamine | QS to pH 6 | QS to pH 6 |
| Water | QS | QS |
| Total | 100.00 | 500.0 |

*The amount of benzoyl peroxide was adjusted to yield a final concentration of 5%.

TABLE 19

Benzoyl peroxide gel formulation 2.

| Ingredient | % w/w | g/batch (Calculated) |
|---|---|---|
| Water | 33.0 | 165.0 |
| Ethanol, Absolute | 30.0 | 150.0 |
| Transcutol ® P | 12.0 | 60.0 |
| Benzoyl Peroxide, 75% (Luperox ® A75FP)* | 6.7 | 33.5 |
| Labrasol ® | 6.0 | 30.0 |
| Cyclomethicone | 5.0 | 25.0 |
| Klucel ® MF Pharm | 1.0 | 5.0 |
| Carbopol ® 974P | 0.6 | 3.0 |
| Phenoxyethanol | 1.0 | 5.0 |
| EDTA, Disodium | 0.1 | 0.5 |
| Trolamine | QS to pH 6 | QS to pH 6 |
| Water | QS | QS |
| Total | 100.0 | 500.0 |

*The amount of benzoyl peroxide was adjusted to yield a final concentration of 5%.

TABLE 20

Cellulose composition for separate combination with each of the benzoyl peroxide formulations.

| Ingredient | % w/w |
|---|---|
| Isopropyl alcohol | 85.5 |
| Hexylene glycol | 10.00 |
| Cyclomethicone | 2.50 |
| Hydroxylpropyl cellulose | 2.00 |

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method of reducing inflammatory and/or noninflammatory lesions present on the skin of a subject, the method comprising:
   providing a first composition and a second composition that are separately stored;
   topically applying to the skin of the subject a composition comprising the first composition and the second composition, wherein the first composition and the second composition are combined prior to and/or during topical application of the combined composition to the skin of the subject,
   wherein the first composition comprises:
   a first viscosity increasing agent;
   at least one polyhydric alcohol;
   at least one buffering agent; and
   water; and
   wherein the second composition comprises:
   a second viscosity increasing agent;
   at least one organic solvent;
   at least one humectant;
   at least one water repellent; and
   a nitric oxide-releasing compound having a diazeniumdiolate functional group, wherein the nitric oxide-releasing compound comprises a NO-releasing co-condensed silica particle,
   thereby reducing inflammatory and/or noninflammatory lesions present on the skin of the subject.

2. The method of claim 1, wherein the first composition has a pH of about.

3. The method of claim 1, wherein the nitric oxide-releasing compound is present in the combined composition in an amount of about 10% by weight of the combined composition or less.

4. The method of claim 1, wherein the combined composition stores and/or releases nitric oxide in an amount of about 0.05% to about 3% by weight of the combined composition.

5. The method of claim 4, wherein the nitric oxide-releasing compound releases nitric oxide in an amount of at least about 50% over a period of time of about 3 hours or less after topical application of the combined composition to skin of a subject.

6. The method of claim 1, wherein the first composition and the second composition are combined in a ratio of about 3:1 to about 0.2:1 of the first composition to the second composition,
wherein the first composition comprises:
the at least one polyhydric alcohol in an amount of about 1% to about 30% by weight of the first composition;
the first viscosity increasing agent in an amount of about 0.1% to about 5% by weight of the first composition;
the at least one buffering agent in an amount of about 0.01% to about 2% by weight of the first composition; and
water in an amount of about 70% to about 99% by weight of the first composition; and
wherein the second composition comprises:
the second viscosity increasing agent in an amount of about 0.5% to about 30% by weight of the second composition;
the at least one organic solvent in an amount of about 50% to about 90 by weight of the second composition;
the at least one humectant in an amount of about 2% to about 20% by weight of the second composition; and
the at least one water repellent in an amount of about 0.5% to about 15% by weight of the second composition.

7. The method of claim 1, wherein the combined composition is cosmetically elegant.

8. The method of claim 1, wherein the number of inflammatory and/or noninflammatory lesions is reduced by about 10% or greater over a defined period of time.

9. The method of claim 1, wherein the reduction in inflammatory and/or noninflammatory lesions is within 12 weeks or less.

10. The method of claim 1, wherein the method reduces noninflammatory lesions on the skin of the subject.

11. The method of claim 1, wherein the method reduces inflammatory lesions on the skin of the subject.

12. The method of claim 1, wherein the method reduces inflammatory and noninflammatory lesions on the skin of the subject.

13. The method of claim 1, wherein the first viscosity increasing agent is selected from the group consisting of a carboxypolymethylene, a polyacrylic polymer, a cellulose ether, a methacrylate, a polyvinylpyrollidone, a polyvinylalcohol, a polyethylene oxide, a polyethylene glycol, a polyvinylalkyl ether-maleic acid copolymer, a carboxy vinyl polymer, a polysaccharide, a gum, a protein, a starch, bentonite, calcium stearate, ceratonia, colloidal silicon dioxide, dextrin, hypromellose, polycarbophil, kaolin, saponite, sorbitan esters, sucrose, sesame oil, tragacanth, potassium alginate, povidone, sodium starch glycolate, phospholipids, and any combination thereof.

14. The method of claim 1, wherein the at least one buffering agent is selected from the group consisting of citric acid, acetic acid, lactic acid, boric acid, succinic acid, malic acid, and any combination thereof.

15. The method of claim 1, wherein the second composition comprises the nitric oxide-releasing compound in an amount of 0.01% to 50% by weight of the second composition.

16. The method of claim 1, wherein the second composition comprises the nitric oxide-releasing compound in an amount of 0.01% to 30% by weight of the second composition.

17. The method of claim 1, wherein the second composition comprises the nitric oxide-releasing compound in an amount of 0.01% to 20% by weight of the second composition.

18. The method of claim 1, wherein the second composition comprises the nitric oxide-releasing compound in an amount of 0.01% to 10% by weight of the second composition.

19. The method of claim 1, wherein the first composition is a hydrogel.

* * * * *

UNITED STATES PATENT AND TRADEMARK OFFICE
CERTIFICATE OF CORRECTION

PATENT NO. : 10,258,564 B2
APPLICATION NO. : 14/771138
DATED : April 16, 2019
INVENTOR(S) : Doxey et al.

Page 1 of 1

It is certified that error appears in the above-identified patent and that said Letters Patent is hereby corrected as shown below:

In the Specification

Column 15, Line 30: Please correct "20%©" to read -- 20% --

Column 18, Line 31: Please correct "R"—N(NONO—X+)—R—Si(OR)3" to read
-- R"—N(NONO—X+)—R'—Si(OR)3 --

Column 49, Line 14: Please correct "(3=0" to read -- β=0 --

Column 50, Line 44: Please correct "19%" to read -- 1.9% --

In the Claims

Column 54, Line 63, Claim 2: Please correct "of about." to read -- of about 3 to about 8. --

Signed and Sealed this
Twentieth Day of August, 2019

Andrei Iancu
*Director of the United States Patent and Trademark Office*